US006150379A

United States Patent [19]
Fatheree et al.

[11] Patent Number: 6,150,379
[45] Date of Patent: Nov. 21, 2000

[54] COMPOUNDS AND COMPOSITIONS AS ANTICOAGULANTS

[75] Inventors: Paul R. Fatheree, San Francisco; Thomas E. Jenkins, La Honda; Martin S. Linsell, San Mateo; Sean G. Trapp, San Francisco; Erik J. Verner, Foster City; Wendy B. Young, San Mateo, all of Calif.

[73] Assignee: Axys Pharmaceuticals, Inc., South San Francisco, Calif.

[21] Appl. No.: 09/193,202

[22] Filed: Nov. 17, 1998

Related U.S. Application Data

[60] Provisional application No. 60/066,536, Nov. 26, 1997.
[51] Int. Cl.[7] ............... A61K 31/4184; A61K 31/4439; C07D 235/18; C07D 401/04
[52] U.S. Cl. ............ 514/338; 514/396; 546/273.4; 548/307.4; 558/300
[58] Field of Search ............ 546/273.4; 514/338, 514/396; 548/307.4; 558/300

[56] References Cited

U.S. PATENT DOCUMENTS

| | | | |
|---|---|---|---|
| 3,105,837 | 10/1963 | Ursprung | 260/309.2 |
| 3,210,370 | 10/1965 | Ursprung | 260/309.2 |
| 3,324,050 | 6/1967 | Joo et al. | 260/2 |
| 4,074,046 | 2/1978 | Mohan | 542/439 |
| 4,940,723 | 7/1990 | Tidwell et al. | 514/396 |
| 5,126,352 | 6/1992 | Ganguly et al. | 514/293 |
| 5,428,051 | 6/1995 | Tidwell et al. | 514/394 |
| 5,552,426 | 9/1996 | Lunn et al. | 514/394 |
| 5,693,515 | 12/1997 | Clark et al. | 435/184 |
| 5,900,371 | 5/1999 | Clark et al. | 435/184 |

FOREIGN PATENT DOCUMENTS

| | | | |
|---|---|---|---|
| 2104196 | 8/1993 | Canada | C07D 403/14 |
| 0 540 051 A1 | 10/1992 | European Pat. Off. | |
| WO 92/20642 | 11/1992 | WIPO | C07C 43/21 |
| WO 94/27594 | 12/1994 | WIPO | A61K 31/30 |
| WO 95/08540 | 3/1995 | WIPO | C07D 235/20 |
| WO 95/19772 | 7/1995 | WIPO | A61K 31/415 |
| WO 97/21437 | 6/1997 | WIPO | |
| WO 98/22619 | 5/1998 | WIPO | |

OTHER PUBLICATIONS

Nagahara et al., "Dibasic (Amidinoaryl) propanoic Acid Derivatives as Novel Blood Coagulation Factor Xa Inhibitors," J. Med. Chem. 37:1200–1207 (1994).
Katz et al., "Design of potent selective zinc–mediated serine protease inhibitors," Nature 39:608–612 (1998).
Caughey et al., "Bis (5–Amidino–2–Benzimidazolyl) Methane and Related Amidines Are Potent, Reversible Inhibitors of Mast Cell Tryptases," J. Pharmacol. Exp. Ther. 264: 676–682 (1993).
Fairley et al., "Structure, DNA Minor Groove Binding, and Base Pair Specificity of Alkyl– and Aryl–Linked Bis (amidinobenzimidazoles) and Bis (amidinoindoles)," J. Med. Chem. 36: 1746–1753 (1993).
Geratz et al., "Streptococcal Cell Wall–Induced Systematic Disease," American Journal of Pathology 139 (4): 921–931 (1991).
Tidwell et al., "Aromatic Amidines: Comparison of Their Ability to Block Respiratory Syncytial Virus Induced Cell Fusion and to Inhibit Plasmin, Urokinase, Thrombin, and Trypsin," J. Med. Chem. 26: 294–298 (1983).
Tidwell et al., "Diarylamadine Derivatives with One or Both of the Aryl Moieties Consisting of an Indole or Indole–like Ring. Inhibitors or Arginine–Specific Esteroproteases" J. Med. Chem. 21 (7): 613–623 (1978).
Tidwell et al., "Suppression of Respiratory Syncytial Virus Infection in Cotton Rats by Bis (5–Amidino–2–Benzimidazolyl) Methane," Antimicrobial Agents and Chemotherapy 26:591–593 (1984).

Primary Examiner—Joseph K. McKane
Assistant Examiner—Taofiq A. Solola
Attorney, Agent, or Firm—Vinit G. Kathardekar; Wayne W. Montgomery

[57] ABSTRACT

The present invention relates to novel biheterocyclic derivatives which are factor Xa inhibitors; the pharmaceutically acceptable salts and N-oxides thereof; their uses as therapeutic agents and the methods of their making.

6 Claims, No Drawings

COMPOUNDS AND COMPOSITIONS AS ANTICOAGULANTS

This application is based on U.S. Provisional Application Serial No. 60/066,536 filed on Nov. 26, 1997.

THE INVENTION

This application relates to compounds and compositions for treating diseases associated with serine protease activity, particularly factor Xa activity.

DESCRIPTION OF THE FIELD

Hemostasis is a function of the physiological processes which initiate and modulate blood coagulation and fibrinolysis. Blood coagulation involves a series of highly complex, inter-related proteolytic events which culminate in the formation of a fibrin clot surrounding the platelet aggregate which makes up the primary hemostatic plug that forms to prevent loss of blood when a vessel is damaged. Fibrin is the product of a proteolytic reaction catalyzed by thrombin, a serine protease, which in turn is the product of a proteolytic activation of prothrombin by factor Xa, also a serine protease. Thrombin also is a potent activator of platelet aggregation.

Factor Xa is converted from inactive factor X by two distinct mechanisms referred to as the intrinsic and extrinsic coagulation pathways. The intrinsic pathway comprises a series of proteolytic reactions catalyzed by factors originating in blood and culminates in the formation of factor IXa. The extrinsic pathway comprises the activation of factor VII by tissue factor, a membrane bound protein, which is available at the site of vessel injury and culminates in the formation of factor VIIa. Factor IXa and factor VIIa, in consert with tissue factor, catalyzes the conversion of factor X to factor Xa. Thus, the formation of factor Xa represents a convergence of the entrinsic and extrinsic pathways in the cascade of events which lead to blood coagulation.

Fibrinolysis is the mechanism by which the platelet aggregate and fibrin clot is dissolved after the vessel injury has healed. The normal physiological condition results in an equilibrium between blood coagulation and anticoagulation mechanisms preventing hemorrhage while maintaining blood fluidity. A pathological condition leading to the occlusion of a blood vessel, i.e., thrombosis, is the equilibrium tipped in the direction of procoagulation. Arterial thrombosis which deprives tissue of oxygen will result in ischemic necrosis of that tissue. Venous thrombosis may result in a pulmonary embolism. Agents which shift the equilibrium towards anticoagulation provide a method for treating and/or preventing thrombosis. Agents which inhibit factor Xa provide a valid pharmacological mechanism for effecting anticoagulation.

The disclosures of these and other documents referred to throughout this application are incorporated herein by reference.

SUMMARY OF THE INVENTION

This application relates to a compound of Formula I:

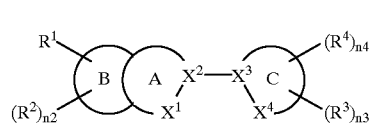

in which:
n2 is 1, 2 or 3;
n3 is 1, 2, 3 or 4;
n4 is 1 or 2;
A together with B comprises a fused heterobicyclic radical containing 8 to 12 annular atoms, wherein each ring contains 5 to 7 annular members, each annular atom optionally is a heteroatom, $X^1$ and $X^2$ are adjacent annular members of an aromatic ring and $X^1$ is a heteroatom moiety selected from —N=, —$NR^5$—, —O— and —S—, wherein $R^5$ is —$R^6$ or —$X^6$—$R^6$, wherein $X^6$ is a linking group containing 1 to 12 contiguous linking atoms and $R^6$ is hydrogen, ($C_{6-14}$)aryl, cyclo($C_{3-14}$)alkyl, hetero($C_{5-14}$)aryl, heterocyclo($C_{3-14}$)alkyl, hetero($C_{8-14}$)polycycloaryl or ($C_{9-14}$)polycycloaryl;

C comprises a heteromonocyclic or fused heteropolycyclic radical containing 5 to 18 annular atoms, wherein each ring contains 5 to 7 annular members, each annular atom optionally is a heteroatom, $X^4$ and $X^5$ are adjacent annular members of an aromatic ring and $X^5$ is a heteroatom moiety selected from —N=, —$NR^5$—, —O— and —S—, wherein $R^5$ is as defined above, and any carbocyclic ketone, thioketone and iminoketone derivative thereof;

$R^1$ is amidino and bonded to any annular carbon atom with an available valence comprising B;

each $R^2$ is independently hydrogen, ($C_{1-3}$)alkyl, ($C_{1-3}$)alkyloxy, ($C_{1-3}$)alkylsulfonyl, ($C_{1-3}$)alkylthio, carboxy, halo, ($C_{2-12}$)heteroalkyl, hydroxy, mercapto or nitro and bonded to any annular atom with an available valence comprising B;

each $R^3$ is independently hydrogen, cyano, halo, nitro, perhalo($C_{1-3}$)alkyl or perhalo($C_{1-3}$)alkyloxy and bonded to any annular atom with an available valence comprising C; and each $R^4$ is independently —$R^6$ or —$X^5$—$R^6$, wherein $X^5$ and $R^6$ are as defined above, and bonded to any annular atom with an available valence comprising C;

wherein aliphatic or alicyclic moieties with an available valence comprising each $X^5$ and $R^6$ optionally are substituted with 1 to 5 substituents independently selected from ($C_{1-6}$)alkyl, ($C_{1-6}$)alkylamino, di($C_{1-6}$)alkylamino, ($C_{1-6}$)alkylcarbamoyl, di($C_{1-6}$)alkylcarbamoyl, ($C_{1-6}$)alkyloxy, ($C_{1-6}$)alkyloxycarbonyl, ($C_{1-6}$)alkylsulfinyl, ($C_{1-6}$)alkylsulfonyl, ($C_{1-6}$)alkylthio, amino, carbamoyl, carboxy, cyano, guanidino, halo, hydroxy, mercapto, perhalo($C_{1-3}$)alkyl, perhalo($C_{1-3}$)alkyloxy and uriedo; and aromatic moieties with an available valence comprising each $X^5$ and $R^6$ optionally are substituted with one to three substituents independently selected from ($C_{1-3}$)alkyl, ($C_{1-3}$)alkylamino, di($C_{1-3}$)alkylamino, ($C_{1-3}$)alkyloxy, ($C_{1-3}$)alkyloxycarbonyl, ($C_{1-3}$)alkylimino, amino, carboxy, cyano, guanidino, halo, hydroxy, perhalo($C_{1-3}$)alkyl and perhalo($C_{1-3}$)alkyloxy; and the N-oxide derivatives, prodrug derivatives, protected derivatives, individual isomers, mixtures of isomers and pharmaceutically acceptable salts thereof.

A second aspect of this invention is a pharmaceutical composition which contains a compound of Formula I or a N-oxide derivative, prodrug derivative, individual isomer, mixture of isomers or pharmaceutically acceptable salt thereof, in admixture with one or more suitable excipients.

A third aspect of this invention is a method of treating a disease in an animal in which contributes to the pathology and/or symptomatology of the disease, which method comprises administering to the animal a therapeutically effective amount of compound of Formula I or a N-oxide derivative, prodrug derivative, individual isomer, mixture of isomers or pharmaceutically acceptable salt thereof.

A fourth aspect of this invention is the processes for preparing compounds of Formula I and or the N-oxide derivatives, prodrug derivatives, protected derivatives, individual isomers, mixture of isomers or pharmaceutically acceptable salts thereof as set forth in "Detailed Description of the Invention".

DETAILED DESCRIPTION OF THE INVENTION

Definitions:

Unless otherwise stated, the following terms used in the specification and claims are defined for the purposes of this application and have the meanings given below:

"Alicyclic moiety" means any saturated or unsaturated, monocyclic or polycyclic portion of a radical and includes cycloalkyl, cycloalkylene, heterocycloalkyl and heterocycloalkylene, as defined in this Section. For example, alicyclic moiety refers to cycloalkyl as well as to the alicyclic portions comprising cycloalkylalkyl, cycloalkyloxy, cycloalkylcarbonyl, cycloalkylcarbamoyl, polycycloaryl, and the like.

"Aliphatic moiety" means any straight or branched, saturated or unsaturated portion of a radical and includes alkyl, alkylene, heteroalkyl and heteroalkylene, as defined in this Section. For example, aliphatic moiety refers to alkyl as well as to aliphatic portions comprising alkyloxy, arylalkyl, alkylcarbamoyl, and the like.

"Alkyl", for the purposes of this application, means a straight or branched, saturated or unsaturated aliphatic radical having the number of carbon atoms indicated, and any carbocyclic ketone, thioketone or iminoketone derivative thereof (e.g., ($C_{1-6}$)alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, 3-oxopentyl, 3-thioxopentyl, 3-iminopentyl, etc.).

"Alkylene" means a saturated or unsaturated divalent radical having the number of carbon atoms indicated and any ketone, thioketone, iminoketone and substituted derivative thereof (e.g., $C_{1-10}$)alkylene includes methylene (—CH$_2$—), ethylene (—CH$_2$CH$_2$—), methylethylene, vinylene, ethynylene, trimethylene (—CH$_2$CH$_2$CH$_2$—), 2-oxotrimethylene (—CH$_2$C(O)CH$_2$—), 2-thiatrimethylene (—CH$_2$C(S)CH$_2$—), 2-iminotrimethylene (—CH$_2$C(NH)CH$_2$—), propenylene (—CH$_2$CH═CH— or —CH═CHCH$_2$—), propanylylidene (═CHCH$_2$CH$_2$—), propendiylene (═CHCH═CH—), 1-aminotetramethylene, pentamethylene, etc.).

"Alkyloxy" means the radical —OR, wherein R is alkyl as defined in this Section, having the number of carbon atoms indicated (e.g., ($C_{1-6}$)alkyloxy includes the radicals methoxy, ethoxy, propoxy, isopropoxy, butoxy, sec-butoxy, isobutoxy, tert-butoxy, vinyloxy, allyloxy, 1-propenyloxy, isopropenyloxy, 1-butenyloxy, 2-butenyloxy, 3-butenyloxy, 2-methylallyloxy, ethynyloxy, 1-propynyloxy, 2-propynyloxy, etc.).

"Alkylsulfonyl" and "alkylthio" mean the radicals —S(O)$_2$R and —SR, respectively, wherein R is alkyl as defined in this Section, having the number of carbon atoms indicated (e.g., ($C_{1-6}$)alkylsulfonyl includes methylsulfonyl, ethylsulfonyl, propylsulfonyl, isopropylsulfonyl, butylsulfonyl, sec-butylsulfonyl, isobutylsulfonyl, tert-butylsulfonyl, vinylsulfonyl, allylsulfonyl, 1-propenylsulfonyl, isopropenylsulfonyl, 1-butenylsulfonyl, 2-butenylsulfonyl, 3-butenylsulfonyl, 2-methylallylsulfonyl, ethynylsulfonyl, 1-propynylsulfonyl, 2-propynylsulfonyl, etc.).

"Amidino" means the radical —C(NH)NH$_2$.

"Amino" means the radical —NH$_2$.

"Animal" includes humans, non-human mammals (e.g., dogs, cats, rabbits, cattle, horses, sheep, goats, swine, deer, etc.) and non-mammals (e.g., birds, etc.).

"Aryl" means an aromatic monocyclic or fused polycyclic radical containing the number of annular carbon atoms indicated, wherein each ring contained therein is comprised of 6 annular members (e.g., ($C_{6-14}$)aryl includes phenyl, naphthalenyl, anthracenyl, phenanthrenyl, etc.).

"Arylene" means an aromatic monocyclic or fused bicyclic divalent radical containing 6 to 10 annular atoms, wherein each ring contained therein is comprised of 6 annular members (e.g., arylene includes 1,4-phenylene, 1,2-phenylene, 1,5-naphthalenylene, 1,8-naphthalenylene, etc.).

"Aromatic moiety" means any aromatic portion of a radical and includes aryl and heteroaryl, as defined in this Section. For example, aromatic moiety refers to aryl as well as the aromatic portions comprising arylalkyl, polycycloaryl, and the like.

"Carbamoyl" means the radical —C(O)NH$_2$.

"Carboxy" means the radical —C(O)OH.

"Cyano" means the radical —CN.

"Cycloalkyl" means a saturated or unsaturated, monocyclic or fused polycyclic radical containing the number of annular carbon atoms indicated, wherein each ring contained therein is comprised of 3 to 8 annular members, and any carbocyclic ketone, thioketone or iminoketone derivative thereof (e.g., ($C_{3-14}$)cycloalkyl includes cyclopropyl, cyclobutyl, cyclopentyl, cyclohexyl, cyclohexenyl, 2,5-cyclohexadienyl, bicyclo[2.2.2]octyl, oxocyclohexyl, dioxocyclohexyl, thiocyclohexyl, 2-oxobicyclo[2.2.1]hept-1-yl, 1-azabicyclo[2.2.2]oct-3-yl, etc.).

"Cycloalkylene" means a saturated or unsaturated, monocyclic or fused bicyclic divalent radical containing 3 to 14 annular atoms, wherein each ring contained therein is comprised of 3 to 8 annular members, and any carbocyclic ketone, thioketone or iminoketone derivative thereof (e.g., cycloalkylene includes cyclopropylene, cyclobutylene, cyclopentylene, cyclohexylene, cyclohexenylene, 2,5-cyclohexadienylene, bicyclo[2.2.2]octylene, oxocyclohexylene, dioxocyclohexylene, thiocyclohexylene, 2-oxobicyclo[2.2.1]hept-1-ylene, 1-azabicyclo[2.2.2]oct-3-ylene, etc.).

"Disease" specifically includes any unhealthy condition of an animal or part thereof and includes an unhealthy condition which may be caused by, or incident to, medical or veterinary therapy applied to that animal, i.e., the "side effects" of such therapy.

"Fused heteropolycyclic radical" includes "fused heterobicyclic radical" and means a heterocyclic radical containing two or more rings having the number of annular members indicated, wherein at least two annular members of one ring are common to a second ring (e.g., a fused heteropolycyclic radical containing from 8 to 18 annular atoms and the carbocyclic ketone and thioketone derivatives thereof includes 1H-benzimidazol-2-yl, 1H-naphtho[2,3-d]imidazol-2-yl, 1H-imidazo[4,5-f]quinolin-2-yl, 1H-imidazo[4,5-b]pyridin-2-yl, 1H-phenanthro[9,10-d]imidazol-2-yl, 1H-imidazo[4,5-g]quinoxalin-2-yl, 2,6-dioxo-2,3,6,7-tetrahydro-1H-purin-8-yl, 2,6-dithioxo-2,3,6,9-tetrahydro-1H-purin-8-yl, 7H-purin-8-yl, 1,6-dihydrocyclopentaimidazol-2-yl, 4-quinolin-2-yl, etc.)

"Guanidino" means the radical —NHC(NH)NH$_2$.

"Halo" means fluoro, chloro, bromo or iodo.

"Heteroatom" means an atom selected from N, O, S and P.

"Heteroatom moiety", unless indicated otherwise, means a moiety selected from —N=, —NR$^7$—, —O—, —S—, —S(O)—, —S(O)$_2$—, —P(O)(OR$^7$)—, wherein R$^7$ is hydrogen or (C$_{1-6}$)alkyl.

"Heteroalkyl" means alkyl, as defined in this Section, except one or more of the carbon atoms indicated is replaced by a heteroatom moiety, as defined in this Section, and any ketone, thioketone or iminoketone derivative thereof (e.g., hetero(C$_{2-12}$)alkyl includes methoxy, ethoxy, ethylthio, 2-(2-methoxyethoxy)ethoxy, 3-methoxymethoxycarbonylmethoxy, 2-(N-ethyl-N-methylamino)ethyl, 2-ethyliminoethyl, ethoxymethoxyphosphoryloxy, etc.).

"Heteroalkylene" means alkylene, as defined in this Section, except one or more of the carbon atoms indicated is replaced by a heteroatom moiety, as defined in this Section, or any suitable combination thereof (e.g., —OS(O)$_2$—, —S(O)$_2$O—, —N(R$^7$)S(O)$_2$—, —S(O)$_2$NR$^7$—, —OP(O)(OR$^7$)O—, and the like), and any ketone, thioketone or iminoketone derivative thereof (e.g., hetero(C$_{2-10}$)alkylene includes azaethylene (—CH$_2$NH—), 2-azapropenylene (—CH$_2$N=CH$_2$—), 1-oxatrimethylene (—CH$_2$CH$_2$O—), 2-oxo-3-azapentamethylene, 3-aza-2-thiopentamethylene, 2-oxa-3-oxopentamethylene, 3-aza-2-iminopentamethylene (—CH$_2$CH$_2$NHC(NH)CH$_2$—), 2,4-aza-2-methyl-3,3-dioxo-3-thiapentamethylene (—CH$_2$NHS(O)$_2$N(CH$_3$)CH$_2$—), 3-hydroxy-2,4-oxa-3-oxo-3-phosphapentamethylene (—CH$_2$OP(O)(OH)OCH$_2$—), 3-aza-2-oxo-4-carboxyhexamethylene, 4-aza-1-oxa-3-oxohexamethylene, 1-thia-3-oxo-4-azahexamethylene, 1-thia-1,1,3-trioxo-4-azahexamethylene (—CH$_2$CH$_2$NHC(O)CH$_2$S(O)$_2$—), 3-aza-4-oxoheptamethylene, 1,4,7-trioxaoctamethylene, 6-aza-1-oxa-2,5-dioxooctamethylene (—CH$_2$CH$_2$NHC(O)CH$_2$CH$_2$C(O)O—), 3-aza-4-oxodecamethylene, etc.).

"Heteroaryl" means an aromatic monocyclic or fused polycyclic divalent radical having the number of annular atoms indicated, wherein each ring contained therein is comprised of 5 to 6 annular members and one or more of the annular atoms is a heteroatom moiety selected from —N=, —NR$^7$—, —O— or —S—, and each ring contained therein is comprised of 5 to 6 annular members (e.g., hetero(C$_{5-14}$)aryl includes thienyl, furyl, pyrrolyl, pyrimidinyl, isoxazolyl, oxazolyl, indolyl, benzo[b]thienyl, isobenzofuranyl, purinyl, isoquinolyl, pterdinyl, perimidinyl, imidazolyl, pyridyl, pyrazolyl, pyrazinyl, quinolyl, etc.).

"Heteroarylene" means an aromatic monocyclic or fused bicyclic divalent radical containing 5 to 10 annular atoms, wherein each ring contained therein is comprised of 5 to 6 annular members and one or more of the annular atoms is a heteroatom moiety selected from —N=, —NR—, —O— or —S—, wherein R is hydrogen or (C$_{1-6}$)alkyl, (e.g., heteroaryl includes thienylene, furylene, pyrrolylene, pyrimidinylene, isoxazolylene, oxaxolylene, indolylene, benzo[b]thienylene, isobenzofuranylene, purinylene, isoquinolylene, imidazolylene, pyridylene, pyrazolylene, pyrazinylene, quinolylene, etc.).

"Heterocycloalkyl" means cycloalkyl, as defined in this Section, except one or more of the annular carbon atoms indicated are replaced by a heteroatom moiety, as defined in this Section, and any carbocyclic ketone, thioketone or iminoketone derivative thereof (e.g., the term heterocyclo(C$_{5-14}$)alkyl includes piperidyl, pyrrolidinyl, pyrrolinyl, imidazolidinyl, quinuclidinyl, morpholinyl, etc.).

"Heterocycloalkylene" means cycloalkylene, as defined in this Section, except one or more of the annular carbon atoms indicated is replaced by a heteroatom moiety, as defined in this Section, and any carbocyclic ketone, thioketone or iminoketone derivative thereof (e.g., the term heterocyclo(C$_{3-14}$)alkylene includes piperidylene, pyrrolidinylene, pyrrolinylene, imidazolidinylene, quinuclidinylene, morpholinylene, etc.).

"Heteropolycycloaryl" means polycycloaryl, as defined below, except one or more of the annular carbon atoms indicated are replaced by a heteroatom moiety, as set defined in this Section, and any carbocyclic ketone, thioketone or iminoketone derivative thereof (e.g., heteropolycyclo(C$_{8-10}$)alkyl includes 3,4-dihydro-2H-quinolinyl, 5,6,7,8-tetrahydroquinolinyl, 3,4-dihydro-2H-[1,8]naphthyridinyl, 2,4-dioxo-3,4-dihydro-2H-quinazolinyl, 3-oxo-2,3-dihydrobenzo[1,4]oxazinyl, etc.).

"Heteropolycycloarylene" means polycycloarylene, as defined below, except one or more of the annular carbon atoms indicated are replaced by a heteroatom moiety, as set defined in this Section, and any carbocyclic ketone, thioketone or iminoketone derivative thereof (e.g., heteropolycyclo(C$_{8-10}$)alkylene includes 3,4-dihydro-2H-quinolinylene, 5,6,7,8-tetrahydroquinolinylene, 3,4-dihydro-2H-[1,8]naphthyridinylene, 2,4-dioxo-3,4-dihydro-2H-quinazolinylene, 3-oxo-2,3-dihydrobenzo[1,4]oxazinylene, etc.).

"Hydroxy" means the radical —OH.

"Imino" means the radical =NH.

"Iminoketone derivative" refers to a radical containing the moiety —C(NR)—, wherein R is hydrogen or (C$_{1-6}$)alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "steroisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 3rd edition, March, Jerry, John Wiley & Sons, New York, 1985). It is understood that the names and illustration used in this application to describe compounds of Formula I are meant to be encompassed all possible stereoisomers. Thus, for example, the name 2-[6-(5-amidino-1H-benzimidazol-2-yl) pyridin-3-ylcarbonylamino]-3-hydroxybutyric acid is meant to include 2S-[6-(5-amidino-1H-benzimidazol-2-yl)pyridin-3-ylcarbonylamino]-3S-hydroxybutyric acid, 2S-[6-(5-amidino-1H-benzimidazol-2-yl)pyridin-3-ylcarbonylamino]-3R-hydroxybutyric acid, 2R-[6-(5-amidino-1H-benzimidazol-2-yl)pyridin-3-ylcarbonylamino]-3R-hydroxybutyric acid and 2R-[6-(5-amidino-1H-benzimidazol-2-yl)pyridin-3-ylcarbonylamino]-3S-hydroxybutyric acid and any mixture, racemic or otherwise, thereof.

"Ketone derivative" refers to a radical containing the moiety —C(O)—.

"Leaving group" has the meaning conventionally associated with it in synthetic organic chemistry, i.e., an atom or group displaceable under alkylating conditions, and includes, halogen, hydroxy, alkyloxy, alkylsulfonloxy (e.g., mesyloxy, ethanesulfonyloxy, etc.), arylsulfonyloxy (e.g., benzenesulfonyloxy and tosyloxy, thienyloxy), dihalophosphinoyloxy, tetrahalophosphaoxy, and the like.

"Linking group" means a saturated or unsaturated divalent radical having the number of contiguous linking atoms indicated, wherein "contiguous linking atoms" refers to the minimum number of connecting atoms linking the free valences, and any substituted, ketone, thioketone or iminoketone derivative thereof. The linking group may contain one or more heteroatom moieties, as defined in this Section, one or more suitable combinations of heteroatom moieties (e.g., —OS(O)$_2$—, —S(O)$_2$O—, —N(R$^7$)S(O)$_2$—, —S(O)$_2$NR$^7$—, —OP(O)(OR$^7$)O—, etc.), alkylene, heteroalkylene, cycloalkylene, heterocycloalkylene, arylene, heteroarylene, polycycloarylene, heteropolycycloarylene, and any combination, ketone, thioketone and iminoketone derivative thereof (e.g., —C(O)—, —C(O)O—, —OC(O)—, —N(R$^7$)C(O)—, —C(O)NR$^7$—, —N(R$^7$)C(O)O—, —OC(O) NR$^7$—, —N(R$^7$)C(O)NR$^7$—, —N(R$^7$)C(N)—, etc.). Hence, a linking group containing 1 to 12 contiguous linking atoms may include one or more heteroatom moieties, one or more suitable combinations of heteroatom moieties and one or more groups selected from (C$_{2-10}$)alkylene, hetero(C$_{2-10}$) alkylene, cycloalkylene, heterocycloalkylene, arylene, heteroarylene, polycycloarylene and heteropolycycloarylene, and any combination thereof (e.g., methylenephen-1,4-ylene (—C$_6$H$_4$CH$_2$— or —CH$_2$C$_6$H$_4$—), methylenepiperazin-1,4-ylene (—N$_2$C$_4$H$_8$CH$_2$— or —CH$_2$N$_2$C$_4$H$_8$—), methyleneoxaphen-1,4-ylene (—OC$_6$H$_4$CH$_2$— or —CH$_2$C$_6$H$_4$O—), etc.).

"Mercapto" means the radical —SH.

"Nitro" means the radical —NO$_2$.

"Optional" or "optionally" means that the subsequently described event or circumstance may or may not occur, and that the description includes instances where the event or circumstance occurs and instances in which it does not. For example, the phrase "optionally are substituted with one to three radicals" means that the group referred to may or may not be substituted in order to fall within the scope of the invention.

"N-oxide derivatives" means a derivatives of compound of Formula I in which nitrogens are in an oxidized state (i.e., O←N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Perhalo(C$_{1-3}$)alkyl" means alkyl, as defined in this Section, except all of the hydrogen atoms are replaced by haloatoms (e.g., trifluoromethyl, etc.).

"Pharmaceutically acceptable salts" means salts of compounds of Formula I which are pharmaceutically acceptable, as defined in this Section, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydoxide. Acceptable organic bases include ethanolamine, diethanolamine, triethanolamine, tromethamine, N-methylglucamine and the like.

"Polycycloaryl" means a fused polycyclic radical containing the number of annular carbon atoms indicated, wherein at least one, but not all, of the fused rings comprising the radical is aromatic and each ring contained therein is comprised of 5 to 6 annular members, and any carbocyclic ketone, thioketone or iminoketone derivative thereof (e.g., polycyclo(C$_{9-10}$)aryl includes indanyl, indenyl, 1,2,3,4-tetrahydronaphthalenyl, 1,2-dihydronaphthalenyl, 2,4-dioxo-1,2,3,4-tetrahydronaphthalenyl, 1,3-dioxo-1,3-dihydro-isoindol-2-yl, etc.).

"Polycycloarylene" means a fused bicyclic divalent radical containing 10 to 12 annular atoms, wherein at least one, but not both, of the fused rings comprising the radical is aromatic and each ring contained therein is comprised of 5 to 6 annular members, and any carbocyclic ketone, thioketone or iminoketone derivative thereof (e.g., polycyclo(C$_{9-10}$)arylene includes indanylene, indenylene, 1,2,3,4-tetrahydronaphthalenylene, 1,2-dihydronaphthalenylene, 2,4-dioxo-1,2,3,4-tetrahydronaphthalenylene, etc.).

"Prodrug derivatives" means derivatives of compounds of Formula I which are converted in vivo to the corresponding non-derivatized form of a compound of Formula I. For example, suitable prodrug derivatives include compounds of Formula I wherein the R$^1$ amidino group is hydroxy- or (C$_{1-6}$)alkyloxy-substituted.

"Protected derivatives" means derivatives of compounds of Formula I in which a reactive site or sites are blocked with protective groups. Protected derivatives of compounds of Formula I are useful in the preparation of compounds of Formula I or in themselves may be active inhibitors of factor Xa. For example, a compound of Formula I may have one or more reactive amino groups. Suitable protecting groups for reactive nitrogen atoms include acetyl, tert-butoxycarbonyl, benzyloxycarbonyl and any other suitable amino protective groups (e.g., see T. W. Greene, *Protective Groups in Organic Synthesis*, John Wiley & Sons, Inc. 1981).

"Therapeutically effective amount" means that amount which, when administered to an animal for treating a disease, is sufficient to effect such treatment for the disease.

"Thioketone derivative" refers to a radical containing the moiety —C(S)—.

"Treatment" or "treating" refers to any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Sulfo" means the radical —S(O)OH.

"Uriedo" means the radical —NHC(O)NH$_2$.

The compounds of Formula I and the intermediates and starting materials used in their preparation are named in accordance with IUPAC rules of nomenclature in which the characteristic groups have decreasing priority for citation as the principle group as follows: acids, esters, amides and amidines. For example, a compound of Formula I in which:

A together with B comprises 5-amidino-1H-benzimidazol-2-yl and C comprises 5-butylpyridin-2-yl is named 2-(5-butylpyridin-2-yl-1H-benzimidazole-5-carboxamidine;

A together with B comprises 5-amidino-1H-benzimidazol-2-yl, C comprises 1-ethoxycarbonylmethyl-5-methyl-1H-imidazol-4-yl is named ethyl 4-(5-amidino-1H-benzimidazol-2-yl)-5-methylimidazol-1-ylacetate;

A together with B comprises 5-amidino-1H-benzimidazol-2-yl, C comprises 4-carboxypyridin-2-yl is named 6-(5-amidino-1H-benzimidazol-2-yl) pyridine-4-carboxylic acid; and A together with B comprises 5-amidino-1H-benzimidazol-2-yl, C comprises 4-benzylcarbamoylpyridin-2-yl is named 6-(5-amidino-1H-benzimidazol-2-yl)-N-benzylpyridine-4-carboxamide.

Certain compounds of Formula I exist in tautomeric equilibrium. For example, compounds of Formula I in which A is 1H-benzimidazol-2-yl exist in equilibrium between tautomers of the following formulae:

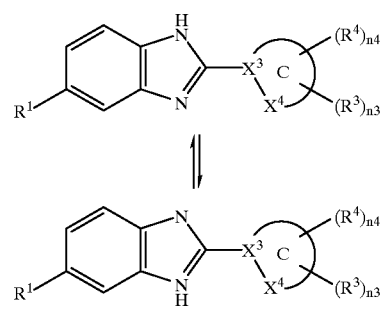

wherein $R^1$ is not hydrogen. Compounds of Formula I which exist as tautomers are named, illustrated or otherwise described in this application as one possible tautomer. However, it is to be understood that the all possible tautomers are meant to be encompassed by such names, illustrations and descriptions. Thus, the name 2-(5-butylpyridin-2-yl)-1H-benzimidazole-5-carboxamidine is meant to include the tautomer 2-(5-butylpyridin-2-yl)-3H-benzimidazole-5-carboxamidine as well.

Presently Preferred Embodiments:

While the broadest definition of this Invention is set forth in the Summary of the Invention, certain aspects of the Invention are preferred. For example, a preferred aspect of the Invention are compounds of Formula I in which:

n2 is 1;

A together with B comprises a fused heterobicyclic radical containing 8 to 10 annular atoms, wherein each ring contains 5 to 6 annular members;

C comprises a heteromonocyclic or fused heteropolycyclic radical containing from 5 to 18 annular atoms, wherein each ring contains 5 to 6 annular atoms;

$R^2$ is hydrogen, $(C_{1-3})$alkyloxy, halo or hydroxy;

each $R^3$ is independently hydrogen, cyano, halo, nitro or perhalo$(C_{1-3})$alkyl; and each $R^4$ and $R^5$ is independently —$R^6$ or —$X^5$—$R^6$, wherein $X^5$ is a linking group containing 1 to 10 contiguous linking atoms and $R^6$ is hydrogen, $(C_{6-10})$aryl, cyclo$(C_{3-6})$alkyl, hetero$(C_{5-10})$aryl, heterocyclo$(C_{5-6})$alkyl or hetero$(C_{8-10})$polycycloaryl.

A further preferred aspect of the Invention is a compound of Formula II:

II

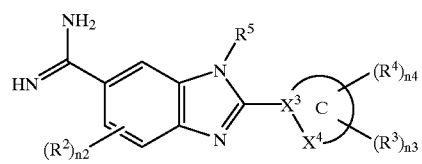

in which C comprises comprises a heteromonocyclic or fused heterobicyclic radical containing 5 to 10 annular atoms.

A further preferred aspect of the Invention is a compound of Formula II in which each $R^4$ and/or $R^5$ is independently —$R^6$, wherein $R^6$ is $(C_{6-14})$aryl, cyclo$(C_{3-14})$alkyl, hetero$(C_{5-14})$aryl, heterocyclo$(C_{3-14})$alkyl, hetero$(C_{8-14})$polycycloaryl or $(C_{9-14})$polycycloaryl, or —$X^5$—$R^6$, wherein $X^6$ is $(C_{1-10})$alkylene, or $(C_{2-10})$heteroalkylene and $R^6$ is hydrogen, $(C_{6-14})$aryl, cyclo$(C_{3-14})$alkyl, hetero$(C_{5-14})$aryl, heterocyclo$(C_{3-14})$alkyl, hetero$(C_{8-14})$polycycloaryl or $(C_{9-14})$polycycloaryl.

A further preferred aspect of the Invention are compounds of Formula II in which C comprises a group selected from 1H-benzimidazol-2-yl, 1H-imidazol-2-yl, 1H-imidazol-4-yl, 2-isoquinol-1-yl, isoquinol-3-yl, pyrazin-2-yl, 1H-pyrazol-3-yl, pyridazin-3-yl, pyridin-2-yl, pyrimidin-2-yl, quinol-2-yl and thiazol-4-yl; particularly in which C comprises pyridin-2-yl.

A further preferred aspect of the Invention are the following compounds of Formula II:

- 6-(5-amidino-1H-benzimidazol-2-yl)-N-[2-(3-bromo-4-methoxyphenyl)ethyl]pyridine-3-carboxamide;
- 2-(5-amidino-1H-benzimidazol-2-yl)imidazol-1-yl-N-[2-(4-chlorophenyl)ethyl]acetamide;
- 2-(1-benzyl-1H-imidazol-2-yl)-1H-benzimidazole-5-carboxamidine;
- 2-(5-butylpyridin-2-yl-1H-benzimidazole-5-carboxamidine;
- 2-(5-amidino-1H-benzimidazol-2-yl)-N-[2-(4-methoxyphenyl)ethyl]pyridine-4-carboxamide;
- 2-(1-butyl-1H-imidazol-2-yl)-1H-benzimidazole-5-carboxamidine;
- 2-{1-[3-(1,3-dioxo-1,3-dihydroisoindol-2-yl)propyl]-5-methyl-1H-imidazol-4-yl}-1H-benzimidazole-5-carboxamidine;
- ethyl 2-(5-amidino-1H-benzimidazol-2-yl)imidazol-1-ylacetate;
- 4-[2-(5-amidino-1H-benzimidazol-2-yl)imidazol-1-yl]-N-[2-(4-chlorophenyl)ethyl]butyramide;
- 6-(5-amidino-1H-benzimidazol-2-yl)-N-[2-(3,4-dichlorophenyl)ethyl]pyridine-5-carboxamide;
- 2-[1-(3-morpholin-4-ylcarbonylpropyl)-1H-imidazol-2-yl]-1H-benzimidazole-5-carboxamidine;
- 2-(5-amidino-1H-benzimidazol-2-yl)imidazol-1-yl-N-[2-(4-hydroxyphenyl)ethyl]acetamide;
- 2-{1-[4-(1,3-dioxo-1,3-dihydroisoindol-2-yl)butyl]-1H-imidazol-2-yl}-1H-benzimidazole-5-carboxamidine;
- 2-(5-amidino-1H-benzimidazol-2-yl)imidazol-1-yl-N-(2-naphth-1-ylethyl)acetamide;
- 2-(5-methyl-1-propyl-1H-imidazol-4-yl)-1H-benzimidazole-5-carboxamidine;
- 6-(5-amidino-1H-benzimidazol-2-yl)-N-[2-(4-methylphenyl)ethyl]pyridine-5-carboxamide; and
- 2-(5-methyl-1-benzyl-1H-imidazol-4-yl)-1H-benzimidazole-5-carboxamidine.

Pharmacology and Utility:

The compounds of this invention are factor Xa inhibitors and, as such, are useful for treating diseases in which factor Xa activity contributes to the pathology and/or symptomatology of the disease. Uses for factor Xa inhibitors include therapy in treating venous thromboembolism (obstruction of a blood vessel with thrombotic material carried by the blood stream from the site of origin to plug another vessel), to reduce the risk of myocardial infarction in patients with unstable angina, to ameliorate further loss of cardiac function in patients with acute myocardial infarction, to reduce the risk of occlusion of saphenous grafts, to reduce periprocedural thrombosis in patients undergoing angioplasty procedures, to reduce the risk of ischemic stroke in patients with atrial fibrillation, to reduce the risk of embolism associated with mechanical heart valves and valvular heart disease, to prevent ischemic strokes in patients with cerebrovascular atherosclerosis, in patients with peripheral vascular disease, and the like.

Suitable in vitro assays for measuring factor Xa activity and the inhibition thereof by test compounds are known. Typically, the assay measures factor Xa induced hydrolysis of a peptide base substrate. Suitable in vivo and ex vivo models for measuring the anti-coagulation activity of test compounds are known to those of ordinary skill in the art. For further details of the assays for measuring factor Xa inhibitor and/or anticoagulant activity see Examples 19, 20 and 21, infra.

Administration and Pharmaceutical Compositions:

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I for anticoagulant therapy may range from 0.1 micrograms per kilogram body weight ($\mu$g/kg) per day to 1 milligram per kilogram body weight (mg/kg) per day, typically 1 $\mu$g/kg/day to 0.1 mg/kg/day. Therefore, a therapeutically effective amount for a 80 kg human patient may range from 10 $\mu$g/day to 10 mg/day, typically 0.1 mg/day to 10 mg/day. In general, one of ordinary skill in the art, acting in reliance upon personal knowledge and the disclosure of this application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.0% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 21.

Chemistry:

Compounds of Formula I in which $X^1$ and $X^2$ are adjacent members of an oxazol-2-yl, 1H-imidazol-2-yl or thiazol-2-yl ring can be prepared by the methods depicted in the following reaction scheme:

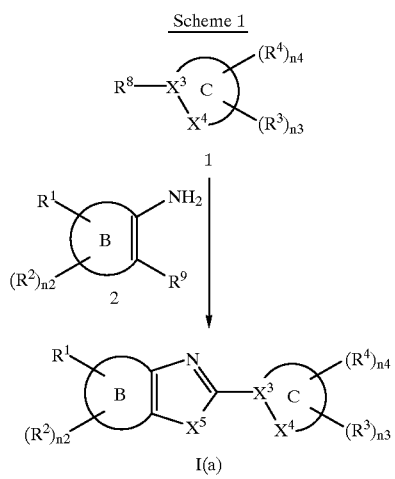

in which $R^8$ is —C(O)L, —CN, —C(NH)L or —CHO, wherein L is a leaving group, $X^6$ is $N(R^5)$, O or S, $R^9$ is —OH, —NHR$^5$ or —SH and n2, n3, n4, B, C, $X^1$, $X^3$, $X^4$, $R^1$, $R^2$, $R^3$, $R^4$ and $R^5$ are as defined in the Summary of the Invention.

Compounds of Formula I in which $X^1$ and $X^2$ are adjacent members of an oxazol-2-yl, 1H-imidazol-2-yl or thiazol-2-yl ring comprising a fused heteropolycyclic radical (Formula I(a)) can be prepared by reacting a compound of Formula 1 with a compound of Formula 2. The reaction may be carried out neat or in an appropriate solvent (e.g., methanol, ethanol) at 160 to 200° C., preferably 170–180° C., and requires 2 to 3 hours to complete (e.g., see Examples 10, 11, 12 and 13, infra.). Reactions proceeding with the acid derivatives of compounds of Formula 1 typically are carried out in the presence of 1,3-dimethyl-3,4,5,6-tetrahydro-2 (1H)-pyrimidinone (DMPU) or polyphosphoric acid. Reactions proceeding with the aldehyde derivatives of Formula 1 typically are carried out in the presence of an oxidizing agent (e.g., nitrobenzene, benzoquinone, etc.).

Compounds of Formula I can be prepared by the methods depicted in the following reaction scheme:

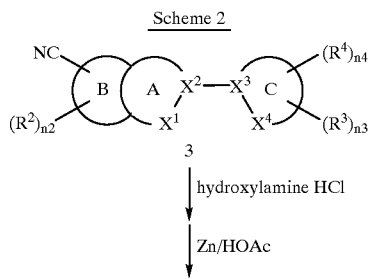

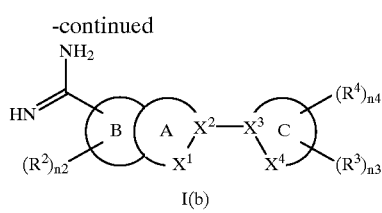

in which n2, n3, n4, A, B, C, $X^1$, $X^2$, $X^3$, $X^4$, $R^2$, $R^3$ and $R^4$ are as defined in the Summary of the Invention.

Compounds of Formula I can be prepared by reacting a corresponding nitrile with hydroxylamine hydrochloride to give a N-hydroxycarboxamidine and then dehydroxylating to give the unsubstituted carboxamidine. The reaction with the hydroxylamine may be carried out in the presence of sodium bicarbonate and in a suitable solvent (e.g., ethanol) at reflux temperature and requires 12 to 18 hours. The dehydroxylation can be effected by reacting the N-hydroxycarboxamidine with zinc in the presence of acetic acid at reflux temperature and requires 3 to 4 hours to complete.

In general, the starting materials required for preparing the compounds of Formula I are either commercially available or can be readily prepared by methods known to those of ordinary skill in the art or as described herein. For example, compounds of Formula 1 in which $R^8$ is —CN and C is pyridin-2-yl can be prepared by reacting a corresponding pyridine derivative with cyanide ion. Such reactions can be carried out by reacting the N-oxide of the pyridine derivative with a suitable cyanide salt (e.g., trimethylsilyl cyanide, cuprous cyanide, etc.) in the presence of a non-nucleophillic base (e.g., trimethylamine) in a suitable solvent (e.g., acetonitrile, N,N-dimethylformamide (DMF), etc.) at 80 to 105° C. and requires 15 to 30 hours to complete (e.g., see Examples 2 and, infra.). In a similar fashion, compounds of Formula I in which $R^8$ is —CN can be prepared from a suitable halo-substituted aromatic derivative (see Examples 3 and 4, infra.).

Compounds of Formula 1 in which $R^8$ is —C(NH)L, wherein L is alkyloxy, can be prepared by reacting a corresponding compound of Formula 1 in which $R^8$ is —CN with the appropriate alcohol in the presence of a catalytic amount of acid (e.g., HCl gas) and in a suitable solvent (e.g., benzene, dioxane, any mixture of solvents, etc.). Typically the reaction is carried out at approximately 0° C., and requires 15 to 20 hours to complete (e.g., see Example 6, infra.).

Compounds of Formula 1 in which $R^8$ is —CHO can be prepared by reacting a suitable heteroaromatic or heteropolycycloaromatic metallic derivative with a formylating agent (e.g., N,N-dimethylformamide). The organometallic derivative can be prepared by reacting a corresponding iodo-substituted derivative with a organometallic base (e.g., t-butyl lithium) in a suitable solvent (e.g., DMF) at low temperatures, typically at −80 to −70° C., for 5 to 10 minutes. The formylating agent is slowly added to the organometallic derivative and the reaction medium is allowed to warm to ambient temperature whereupon the reaction will proceed to completion in 15 to 30 minutes.

Additional Processes for Preparing Compounds of Formula I:

Compounds of Formula I in which $R^4$ or $R^5$ comprises —$X^7$C(O)NR$^7$X$^8$R$^6$ can be prepared by reacting a corresponding compound of Formula I in which $R^4$ or $R^5$ comprises —$X^7$C(O)OH with a compound having the formula $R^6X^8NHR^7$, wherein $X^7$ and $X^8$ are linking groups containing n7 and n8 contiguous linking atoms, respectively, wherein the sum of n7 and n8 is 0 to 10, $R^7$ is hydrogen or $(C_{1-6})$alkyl and $R^6$ is as defined in the Summary of the Invention. The reaction typically is carried out in the presence of 1-hydroxybenzotriazole (HOBT) and a coupling agent (e.g., benzotriazol-1-yloxytrispyrrolidinophosphonium hexafluorophosphate (PyBOP), 1-(3-dimethylaminopropyl)-3-ethylcarbodiimide (EDCI), 1,1-carbonyldiimidazole, etc.) and a non-nucleophillic base (e.g., N-methylmorpholine, N,N-diisopropylethylamine, etc.) and in a suitable solvent (e.g., N,N-dimethylformamide (DMF), tetrahydrofuran (THF), dichloromethane, etc., preferably DMF) at 20 to 25° C. and requires 12 to 24 hours to complete (e.g., see Example 16, infra.).

Compounds of Formula I in which $R^4$ or $R^5$ comprises $-X^7NR^7C(O)X^8R^6$ can be prepared by reacting a corresponding compound of Formula I in which $R^4$ or $R^5$ comprises $-X^7NHR^7$ with a compound having the formula $R^6X^8C(O)OH$, wherein $X^7$ and $X^8$ are linking groups containing n7 and n8 contiguous linking atoms, respectively, wherein the sum of n7 and n8 is 0 to 10, $R^7$ is hydrogen or $(C_{1-6})$alkyl and $R^6$ is as defined in the Summary of the Invention. The reaction typically is carried out in the presence of a coupling agent (e.g., PyBOP, EDCI, 1,1-carbonyldiimidazole, etc.) and a non-nucleophillic base (e.g., N-methylmorpholine, N,N-diisopropylethylamine, etc.) and in a suitable solvent (e.g., DMF, THF, dichloromethane, etc., preferably DMF) at 20 to 25° C. and requires 6 to 24 hours to complete.

Compounds of Formula I in which $R^4$ or $R^5$ comprises $-X^7NR^7S(O)_2X^8R^6$ can be prepared by reacting a corresponding compound of Formula I in which $R^4$ or $R^5$ comprises $-X^7NHR^7$ with a compound having the formula $R^6X^8S(O)_2Cl$, wherein $X^7$ and $X^8$ are linking groups containing n7 and n8 contiguous linking atoms, respectively, wherein the sum of n7 and n8 is 0 to 10, $R^7$ is hydrogen or $(C_{1-6})$alkyl and $R^6$ is as defined in the Summary of the Invention. The reaction typically is carried out in the presence of a non-nucleophillic base (e.g., N-methylmorpholine, N,N-diisopropylethylamine, etc.) and in a suitable solvent (e.g., DMF, THF, dichloromethane, etc., preferably DMF) at 20 to 25° C. and requires 12 to 24 hours to complete.

Compounds of Formula I in which $R^4$ or $R^5$ comprises $-X^7NR^7CH_2X^8R^6$ can be prepared by reacting a corresponding compound of Formula I in which $R^4$ or $R^5$ comprises $-X^7NHR^7$ with a compound having the formula $R^6X^8C(O)H$ under reducing conditions, wherein $X^7$ and $X^8$ are linking groups containing n7 and n8 contiguous linking atoms, respectively, wherein the sum of n7 and n8 is 0 to 10, $R^7$ is hydrogen or $(C_{1-6})$alkyl and $R^6$ is as defined in the Summary of the Invention. The reaction typically is carried out in the presence of a reducing agent (e.g., sodium cyanoborohydride) and in a suitable solvent (e.g., methanol) at 20 to 25° C. and requires 12 to 24 hours to complete.

Compounds of Formula I may be prepared as pharmaceutically acceptable acid addition salts by reacting the free base forms of a compound of Formula I with a pharmaceutically acceptable inorganic or organic acid. Alternatively, the pharmaceutically acceptable base addition salts of compounds of Formula I may be prepared by reacting the free acid forms of compounds of Formula I with pharmaceutically acceptable inorganic or organic bases. Inorganic and organic acids and bases suitable for the preparation of the pharmaceutically acceptable salts of compounds of Formula I are set forth in the definitions section of this application. Alternatively, the salt forms of the compounds of Formula I may be prepared using salts of the starting materials or intermediates.

The free acid or free base forms of the compounds of Formula I can be prepared from the corresponding base addition salt or acid addition salt form. For example, compounds of Formula I in an acid addition salt form may be converted to the corresponding free base by treating with a suitable base (e.g., ammonium hydroxide solution, sodium hydroxide, etc.). Compounds of Formula I in a base addition salt form may be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable inert organic solvent (e.g., a halogenated such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, etc.) in an suitable inert organic solvent (e.g., acetonitrile, ethanol, aqueous dioxane, etc.) at 0 to 80° C.

Prodrug derivatives of the compounds of Formula I can be prepared by methods known to those of ordinary skill in the art (e.g., for further details see Saulnier et al. (1994), *Bioorganic and Medicinal Chemistry Letters*. 4:1985).

Protected derivatives of the compounds of Formula I can be made by means known to those of ordinary skill in the art. A detailed description of the techniques applicable to the creation of protective groups and their removal can be found in T. W. Greene, *Protective Groups in Organic Synthesis*, John Wiley & Sons, Inc. 1981.

Compounds of Formula I can be prepared as their individual stereoisomers by reacting a racemic mixture of the compound with an optically active resolving agent to form a pair of diastereomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/ resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixtures can be found in Jean Jacques, Andre Collet, Samuel H. Wilen, Enantiomers, Racemates and Resolutions, John Wiley & Sons, Inc. (1981).

In summary, an aspect of this invention is a process for preparing compounds of Formula I, which process comprises:

(a) reacting a compound of Formula 1:

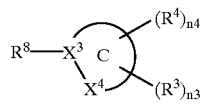

1 with a compound of Formula 2:

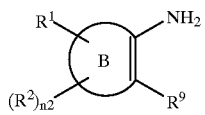

2 in which $R^8$ is —C(O)L, —CN, —C(NH)L or —CHO, wherein L is a leaving group, $R^9$ is —OH, —$NHR^5$ or —SH and n2, n3, n4, B, C, $X^3$, $X^4$, $R^1$, $R^2$, $R^3$, $R^4$ and $R^5$ are as defined in the summary of the Invention;

(b) reacting a compound of Formula 3:

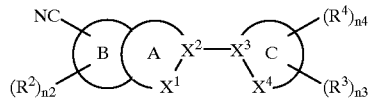

3 in which n2, n3, n4, A, B, C, $X^1$, $X^2$, $X^3$, $X^4$, $R^2$, $R^3$ and $R^4$ are as defined in the summary of the Invention, with hydroxylamine hydrochloride to give a corresponding N-hydroxycarboxamidine and then dehydroxylating;

(c) optionally further reacting a compound of Formula I in which $R^4$ or $R^5$ comprises —$X^7$C(O)OH with a compound having the formula $R^6X^8NHR^7$ to give a compound of Formula I in which $R^4$ or $R^5$ comprises —$X^7$C(O)$NR^7X^8R^6$, wherein $X^7$ and $X^8$ are linking groups containing n7 and n8 contiguous linking atoms, respectively, wherein the sum of n7 and n8 is 0 to 10, $R^7$ is hydrogen or ($C_{1-6}$)alkyl and $R^6$ is as defined in the Summary of the Invention;

(d) optionally further reacting a compound of Formula I in which $R^4$ or $R^5$ comprises —$X^7NHR^7$ with a compound having the formula $R^6X^8$C(O)OH to give a compound of Formula I in which $R^4$ or $R^5$ comprises —$X^7NR^7$C(O)$X^8R^6$, wherein $X^7$ and $X^8$ are linking groups containing n7 and n8 contiguous linking atoms, respectively, wherein the sum of n7 and n8 is 0 to 10, $R^7$ is hydrogen or ($C_{1-6}$)alkyl and $R^6$ is as defined in the Summary of the Invention;

(e) optionally further reacting a compound of Formula I in which $R^4$ or $R^5$ comprises —$X^7NHR^7$ with a compound having the formula $R^6X^8S(O)_2Cl$ to give a compound of Formula I in which $R^4$ or $R^5$ comprises —$X^7NR^7S(O)_2X^8R^6$, wherein $X^7$ and $X^8$ are linking groups containing n7 and n8 contiguous linking atoms, respectively, wherein the sum of n7 and n8 is 0 to 10, $R^7$ is hydrogen or ($C_{1-6}$)alkyl and $R^6$ is as defined in the Summary of the Invention;

(f) optionally further reacting a compound of Formula I in which $R^4$ or $R^5$ comprises —$X^7NHR^7$ with a compound having the formula $R^6X^8$C(O)H under reducing conditions to give a compound of Formula I in which $R^4$ or $R^5$ comprises —$X^7NR^7CH_2X^8R^6$, wherein $X^7$ and $X^8$ are linking groups containing n7 and n8 contiguous linking atoms, respectively, wherein the sum of n7 and n8 is 0 to 10, $R^7$ is hydrogen or ($C_{1-6}$)alkyl and $R^6$ is as defined in the Summary of the Invention;

(g) optionally further converting a compound of Formula I into a pharmaceutically acceptable salt;

(h) optionally further converting a salt form of a compound of Formula I to non-salt form;

(i) optionally further converting an unoxidized form of a compound of Formula I into a pharmaceutically acceptable N-oxide;

(j) optionally further an N-oxide form of a compound of Formula I its unoxidized form;

(k) optionally further converting a non-derivatized compound of Formula I into a pharmaceutically prodrug derivative;

(l) optionally further converting a prodrug derivative of a compound of Formula I to its non-derivatized form; and (m) optionally further separating a mixture of stereoisomers of a compound of Formula I to give a single stereoisomer.

In any of the above processes each are as defined in their broadest definitions set forth in the Summary of the Invention, with the processes applying particularly well to the presently preferred embodiments.

EXAMPLES

Example 1

4,5-Diamino-2-fluorobenzonitrile

A mixture of potassium nitrate (73.2 g, 0.718 mmol, 2 eq) and concentrated sulfuric acid (350 mL) was cooled to 0° C. and 2,4-difluorobenzonitrile was added in portions over 10 to 15 minutes. The mixture was stirred for 30 minutes and then poured onto ice to give a precipitate. The precipitate was isolated by filtration, washed with water and lyophilized to provide 2,4-difluoro-5-nitrobenzonitrile (50 g, 0.28 mol) as an off-white solid; PB-CI/MS: 185=($MH^+$); $^1$H-NMR (300 Mhz, DMSO-$d_6$): 8.093(t, 1H), 8.982(t, 1H).

A mixture comprising 2,4-difluoro-5-nitrobenzonitrile (9.03 g, 0.049 mol) and ethanol (10–15 mL) was stirred at ambient temperature while concentrated ammonium hydroxide (40 mL) was slowly added to give a precipitate. The precipitate was isolated by filtration and lyophilized to give 4-amino-2-fluoro-5-nitrobenzonitrile (7.84 g, 0.043 mol) as an off-white solid; PB-CI/MS: 182=($MH^+$); $^1$H-NMR (300 Mhz, DMSO-$d_6$): 6.856(d, 1H), 8.22(bs, 2H), 8.577(d, 1H). A mixture of 4-amino-2-fluoro-5-nitrobenzonitrile (3 g, 0.017 mol), PtO2 (≈300 mg) and methanol (20 mL)was hydrogenated (1 atm) for approximately 12 hours, filtered over celite and concentrated to dryness to provide 4,5-diamino-2-fluorobenzonitrile (2.5 g, 0.017 mol) as a brown solid PB-CI/MS: 152=($MH^+$); $^1$H-NMR (300 Mhz, DMSO-$d_6$): 4.7(bs, 2H), 5.863(bs, 2H), 6.375(d, 1H), 6.56(d, 1H).

Example 2

4-Methylpyridine-2-carbonitrile, a Compound of Formula 1 in which C Comprises 4-methylpyridin-2-yl and $R^8$ is —CN Triethylamine (13.4 mL, 91.9 mmol) and trimethylsilyl cyanide (25 mL, 187.5 mmol) were added sequentially to a solution comprising 4-methylpyridine N-oxide (5 g, 45.8 mmol) and acetonitrile (20 mL). The mixture was heated at reflux for 24 hours, cooled and diluted with methylene chloride (150 mL). Saturated sodium bicarbonate solution (100 mL) was added slowly to the mixture and then the aqueous layer was separated and extracted with methylene chloride (100 mL). The combined organic layers were washed with water (2×150 mL), dried (MgSO$_4$) and concentrated under reduced pressure. The residue was crystallized from ethyl acetate/hexanes to provide 4-methylpyridine-2-carbonitrile (3.5 g, 29.6 mmol) as a dark solid, $^1$H-NMR (300 Mhz, DMSO-d$_6$): 2.4 (s, 3H), 7.6 (d, 1H, J=5 Hz), 7.8 (s, 1H), 8.6 (d, 1H, J=5 Hz), MS (ESI), Calculated for C$_7$H$_6$N$_2$: 228.24, Found (MH$^+$): 119.

Proceeding as in Example 2, but substituting other pyridine N-oxide derivatives for 4-methylpyridine N-oxide, provided the following compounds of Formula 1:

2-cyanopyridine-4-carboxylic acid; $^1$H-NMR (300 Mhz, DMSO-d$_6$): 8.2 (d, 1H, J=4.8 Hz), 8.4 (s, 1H), 9 (d, 1H, J=4.8 Hz); MS (CI), Calculated for C$_7$H$_4$N$_2$O$_2$: 148.14, Found (MH$^+$): 149; and 6-cyanopyridine-3-carboxylic acid; $^1$H-NMR (300 Mhz, DMSO-d$_6$): 8.2 (d, 1H, J=8 Hz), 8.4 (d, 1H, J=8 Hz), 9.1 (s, 1H); MS (CI), Calculated for C$_7$H$_4$N$_2$O$_2$: 148.1; Found (MH$^+$): 149.

Example 3

5-Nitropyridine-2-carbonitrile, a Compound of Formula 1 in which C Comprises 5-nitropyridin-2-yl and R$^8$ is —CN A mixture comprising 2-bromo-5-nitropyridine (5.6 g, 27.7 mmol), cuprous cyanide (2.5 g, 27.4 mmol) and DMF (5 mL) was heated at 105° C. for 2.5 hours, cooled and diluted with methylene chloride (200 mL). The mixture was stirred 20 minutes, filtered and concentrated under reduced pressure. The residue was dissolved in methylene chloride and the solution was washed sequentially with 2N sodium hydroxide (150 mL), 7M ammonium hydroxide (150 mL) and water (150 mL), dried (MgSO$_4$), filtered and concentrated under reduced pressure to provide 5-nitropyridine-2-carbonitrile (3.14 g, 21 mmol) as a yellow oil. $^1$H-NMR (300 Mhz, DMSO-d$_6$): 8.4 (d, 1H), 8.8 (d, 1H), 9.5 (s, 1H); MS (EI); Calculated for C$_6$H$_3$N$_3$O$_2$, 149.1, Found (MH$^+$): 149.

Proceeding as in Example 3, but substituting 2,5-dibromopyridine for 2-bromo-5-nitropyridine, provided 5-bromopyridine-2-carbonitrile; $^1$H-NMR (300 Mhz, DMSO-d$_6$): 7.6 (d, 1H, J=5 Hz), 8.0 (dd, 1H, J=2 Hz, 5 Hz), 8.1 (d, 1H, J=2 Hz); MS (CI), Calculated for C$_6$H$_3$N$_2$Br, 183.0, Found (MH$^+$): 185.

Example 4

5-Phenylpyridine-2-carbonitrile, a Compound of Formula 1 in which C Comprises 5-phenylpyridin-2-yl and R$^8$ is —CN A mixture comprising 5-bromopyridine-2-carbonitrile (0.09 g, 0.49 mmol), phenyl boronic acid (0.12 g, 0.98 mmol), 2M sodium carbonate ((0.98 mL, 1.96 mmol), tetrakis(tritylphosphanyl)palladium (0.06 g, 0.049 mmol), benzene (2 mL) and ethanol (2 mL) was heated at reflux for 1 hour and then partitioned between ethyl acetate and water. The organic layer was separated, washed with water, dried (MgSO$_4$) and concentrated. The residue was purified by silica gel chromatography (25% ethyl acetate/hexanes) to provide 5-phenylpyridine-2-carbonitrile (0.12 g, 0.67 mmol). MS (CI), Calculated for C$_{12}$H$_8$N$_2$, 180.2, Found (MH$^+$): 182.

Example 5

Methyl 6-cyanopyridine-3-carboxylate, a Compound of Formula 1 in which C Comprises 3-methoxycarbonylpyridin-2-yl and R$^8$ is —CN Potassium carbonate (6.1 g, 43.9 mmol) and methyl iodide (21 mL, 338 mmol) were added sequentially to a solution comprising 6-cyanopyridine-3-carboxylic acid (5 g, 33.8 mmol) in acetone (300 mL). The mixture was heated at reflux for 15 hours and concentrated under reduced pressure. The residue was partioned between ether and saturated sodium bicarbonate. The organic layer was washed with water, dried (MgSO$_4$), filtered and concentrated under reduced pressure to provide methyl 6-cyanopyridine-3-carboxylate (4.4 g, 27.1 mmol) as a tan solid. $^1$H-NMR (300 Mhz, DMSO-d$_6$): 3.9 (s, 3H), 8.2 (d, 1H, J=7.5 Hz), 8.5 (d, 1H, J=7.5 Hz), 9.2 (s, 1H).

Example 6

2-(C-Ethoxyiminomethyl)pyridine-4-carboxylic acid, a Compound of Formula 1 in which C Comprises 4-carboxypyridin-2-yl and R$^8$ is —C(NH)L, wherein L is Ethoxy Anhydrous ethanol (0.1 mL) was added to a solution comprising 2-cyanopyridine-2-carboxylic acid (0.21 g, 1.4 mmol), benzene (15 mL) and dioxane (6 mL). The mixture was cooled to 0° C. under nitrogen and then bubbled with HCl gas for 20 minutes. The reaction container was sealed and vented after 15 hours. The mixture was diluted with anhydrous ether to give a precipitate. The precipitate was isolated by filtration, washed with ether and dried to provide 2-(C-ethoxyiminomethyl)pyridine-4-carboxylic acid (0.21 g, 0.91 mmol) as a white solid. $^1$H-NMR (300 Mhz, DMSO-d$_6$): 1.5 (t, 3H, J=7.2 Hz), 4.7 (q, 4H, J=7.2 Hz), 8.2 (d, 1H, J=4.9 Hz).

Proceeding as in Example 6, but substituting methyl 6-cyanopyridine-3-carboxylate for 2-cyanopyridine-2-carboxylic acid provided methyl 6-(C-ethoxyiminomethyl)pyridine-3-carboxylate; $^1$H-NMR (300 Mhz, DMSO-d$_6$): 1.5 (t, 3H, J=7 Hz), 3.9 (s, 1H), 4.7 (q, 2H, J=7 Hz), 8.3 (d, 1H, J=8 Hz), 8.6 (d, 1H), J=8 Hz), 9.2 (s, 1H).

Example 7

5-Propoxypyridine-2-carboxaldehyde, a Compound of Formula 1 in which C Comprises 5-propoxypyridin-2-yl and R$^8$ is —CHO A mixture comprising pyridin-3-ol (10 g, 105 mmol), sodium iodide (15.8 g, 105 mmol), sodium hydroxide (4.2 g, 105 mmol) and methanol (285 mL) was cooled to 0° C. and then a 4% solution of aqueous sodium hypochlorite (196 g) was added dropwise over 2 hours. The mixture was allowed to warm to ambient temperature, stirred for 24 hours, diluted slowly with 10% sodium thiosulfate (100 mL) and then extracted with methylene chloride (2×200 mL). The combined extracts were dried (MgSO$_4$), filtered and concentrated under reduced pressure. The residue was triturated with hot ethyl acetate (50 mL) and the solid was isolated and dried to provide 6-iodopyridin-3-ol (4.8 g, 20.8 mol) as a white solid. $^1$H-NMR (300 Mhz, DMSO-d$_6$): 7.2 (m, 2H), 7.8 (s, 1H), 10.8 (bs, 1H); MS (ESI); Calculated for C$_5$H$_4$NIO, 221.0, Found (MH$^+$): 221.7.

Iodopropane (0.18 mL, 1.8 mmol) was added dropwise to a mixture comprising 6-iodopyridin-3-ol (0.32 g, 1.14 mmol), potassium bicarbonate (0.23 g, 1.7 mmol) and DMF (2 mL). The mixture was heated at 80° C. for 1 hour, cooled and diluted with methylene chloride and water. The aqueous layer was separated and extracted with methylene chloride (20 mL). The combined organic layers were washed with water 30 mL, dried (MgSO$_4$) and concentrated under reduced pressure to provide 2-iodo-5-propoxypyridine. MS (ESI); Calculated for C$_8$H$_{10}$NIO, 266.1, Found (MH$^+$): 222.

A mixture comprising 2-iodo-5-propoxypyridine (0.27 g, 1 mmol) and THF (10 mL) was cooled to −78° C. and then tert-butyl lithium (1.3 mL, 1.7 M in pentane, 2.1 mmol) was added dropwise to give an orange slurry. The slurry was cooled to −78° C. and stirred for 5 minutes and then anhydrous N,N-dimethylformamide (0.4 mL, 5 mmol) was added dropwise. The mixture was allowed to warm to ambient temperature, stirred 20 minutes and then poured into a mixture comprising ethyl acetate and water. The mixture was washed with water, dried (MgSO$_4$), filtered and concentrated under reduced pressure to provide 5-propoxypyridine-2-carboxaldehyde (0.2 g, 1.3 mmol) as a dark oil. $^1$H-NMR (300 Mhz, CD$_3$OD): 1.1 (t, 3H), 1.9 (m, 2H), 4.1 (t, 2H), 7.5 (m, 2H), 8.4 (m, 1H), 10.5 (s, 2H); MS (CI); Calculated for C$_9$H$_{11}$NO$_2$, 165.2, Found (MH$^+$): 166.

Example 8

Ethyl 4-formyl-5-methylimidazol-1-ylacetate, a Compound of Formula 1 in which C Comprises 1-ethoxycarbonylmethyl-5-methyl-1H-imidazol-4-yl and R$^8$ is —CHO A 30% solution of sodium hydride (1.2 g, 32.6 mmol) was washed with pet ether (3×15 mL) and then slurried in THF (30 mL) under nitrogen. The slurry was cooled to 0° C. and 5-methylimidazole-4-carboxaldehyde (3 g, 27.2 mmol) was added in two portions. The mixture was stirred at ambient temperature for 2 hours, cooled to 0° C. and ethyl bromacetate (4.5 mL, 38.1 mmol) was added dropwise. The mixture was stirred at ambient temperature for 40 minutes and partitioned between ethyl acetate and water. The organic layer was isolated, washed with water, dried (MgSO$_4$), filtered and concentrated under reduced pressure. The residue was triturated with pet ether to provide ethyl 4-formyl-5-methylimidazol-1-ylacetate (5.3 g, 27 mmol) as a yellow solid. $^1$H-NMR (300 Mhz, DMSO-d$_6$): 1.2 (t, 3H), 2.4 (s, 3H), 4.2 (q, 2H), 5.0 (s, 2H), 7.8 (s, 1H), 9.8 (s, 1H).

Example 9

4-Amino-3-phenethylaminobenzamidine, a Compound of Formula 2 in which B Together with the Vinylene Moiety to which it is Fused Comprises 5-amidino-1,2-phenylene and R$^9$ is —NHR$^5$, wherein R$^5$ is 2-phenylethyl A mixture comprising 3-methoxy-4-nitrobenzonitrile (1 g, 5.6 mmol), phenethylamine hydrochloride (1.8 g, 11.2 mmol), 50% sodium hydroxide (0.9 g, 11.2 mmol) and DMSO (3 mL) was heated at 100° C. for 3.5 hours, cooled and poured into a solution of 1N hydrochloric acid (200 mL, 0° C.). The mixture was stirred for 20 minutes to give a precipitate. The precipitate was collected and recrystallized from hot ethanol to provide 4-nitro-3-phenethylaminobenzonitrile (0.78 g, 2.9 mmol) as orange crystals. MS (CI), Calculated for C$_{15}$H$_{13}$N$_3$O$_2$, 267.3, Found (MH$^+$): 282. A mixture comprising 4-nitro-3-phenethylaminobenzonitrile (0.75 g, 2.8 mmol), palladium on carbon (100 mg) and 1:1 methanol/THF (100 mL) was hydrogenated under 1 atm for 3 hours, filtered and concentrated under reduced pressure to provide 4-amino-3-phenethylaminobenzonitrile (0.68 g, 2.8 mmol) as a tan solid.

4-Amino-3-phenethylaminobenzonitrile (0.72 g, 3 mmol) was azeotroped twice with benzene and then dissolved in benzene (15 mL) under nitrogen. The solution was combined with ethanol (0.86 mL, 14.7 mmol) and the mixture was cooled to 0° C. and bubbled with HCl gas for 25 minutes. The reaction container was sealed and the mixture was stirred for 20 hours at ambient temperature. The container was vented and the mixture was diluted with anhydrous ether (30 mL) to give a precipitate. The precipitate was isolated by filtration to provide ethyl 4-amino-3-phenethylaminobenzamidine hydrochloride (0.7 g, 2.2 mmol) as a tan solid. MS (CI), Calculated for C$_{17}$H$_{21}$N$_3$O, 283.4, Found (MH$^+$): 284.

A mixture comprising ethyl 4-amino-3-phenethylaminobenzamidine hydrochloride (0.68, 2.1 mmol) and 2M ammonia in ethanol (20 mL) was heated at 90° C. in a sealed reaction container for 2.5 hours. The container was vented and the mixture was concentrated under reduced pressure to provide 4-amino-3-phenethylaminobenzamidine hydrochloride (0.4 g, 1.2 mmol) as a brown foam. $^1$H-NMR (300 Mhz, DMSO-d$_6$): 2.9 (t, 2H), 3.4 (m, 2H), 5.1 (m, 1H), 5.8 (s, 2H), 6.6 (d, 1H), 6.8 (s, 1H), 7.1 (d, 1H), 7.3 (m, 5H), 8.6 (s, 2H), 8.7 (s, 2H).

Example 10

2-(5-Butylpyridin-2-yl-1H-benzimidazole-5-carboxamidine (Compound 1), a Compound of Formula I in which A Together with B Comprises 5-amidino1H-benzimidazol-2-yl, and C Comprises 5-butylpyridin-2-yl A mixture comprising 5-butylpyridine-2-carboxylic acid (4 g, 22.3 mmol), 3,4-diaminobenzamidine hydrochloride (3.8 g, 20.1 mmol) and polyphosphoric acid (15 mL) was heated at 185° C. for 2.5 hours, cooled and then poured into water (100 mL). The mixture was cooled to 0° C. and neutralized with 50% sodium hydroxide to give a precipitate. The precipitate was isolated by filtration, washed with water and stirred with saturated sodium bicarbonate solution for 30 minutes. The precipitate was again isolated by filtration, washed with water and dissolved in 6N hydrochloric acid (40 mL). The solution was poured into stirring acetone (4 mL) to give a precipitate. The precipitate was dissolved in hot methanol (30 mL) and the solution was diluted sequentially with ethyl acetate (50 mL), ether (200 mL) and acetone (100 mL) to give a tan precipitate. The precipitate was isolated by filtration, washed with acetone (200 mL) and dried to provide 2-(5-butylpyridin-2-yl-1H-benzimidazole-5-carboxamidine (3.45 g, 11.8 mmol). $^1$H-NMR (300 Mhz, DMSO-d$_6$): 0.8 (m, 3H), 1.3 (m, 2H), 1.6 (m, 2H), 2.7 (m, 2H), 7.85 (m, 2H), 7.97 (dd, 1H, J=8.1 Hz, 1.5 Hz), 8.23 (s, 1H), 8.55 (d, 1H, J=8.1 Hz), 8.69 (d, 1H, J=1.5 Hz); MS (ESI); Calculated for C$_{17}$H$_{19}$N$_5$: 293.3; Found (MH$^+$): 294.1.

Proceeding as in Example 10, but substituting other carboxylic acid derivatives for 5-butylpyridine-2-carboxylic acid, provided the following compounds of Formula I:

2-quinoxalin-2-yl-3H-benzimidazole-5-carboxamidine (Compound 2); MS (ESI), Calculated for C$_{16}$H$_{12}$N$_6$: 288.3; Found (MH$^+$): 288.7;

2-pyridin-2-yl-3H-benzimidazole-5-carboxamidine MS (ESI), Calculated for C$_{13}$H$_{11}$N$_5$: 237.10 Found (MH$^+$): 237.9 (Compound 3);

2-isoquinolin-1-yl-1H-benzimidazole-5-carboxamidine (Compound 4); MS (BIOION), Calculated for $C_{17}H_{13}N_5$: 287.32, Found (MH$^+$): 288;

2-isoquinolin-3-yl-1H-benzimidazole-5-carboxamidine (Compound 5); MS (BIOION), Calculated for $C_{17}H_{13}N_5$: 287.32, Found (MH$^+$): 287.7;

2-(3-hydroxypyridin-2-yl)-1H-benzimidazole-5-carboxamidine (Compound 6); MS (ESI), Calculated for $C_{13}H_{11}N_5O$: 253.26, Found (MH$^+$): 254.2;

2-(5-methylpyrazin-2-yl)-1H-benzimidazole-5-carboxamidine (Compound 7); MS (ESI), Calculated for $C_{13}H_{12}N_6$: 252.11, Found (MH$^+$): 252.7;

2-(2-methylthiazol-4-yl)-1H-benzimidazole-5-carboxamidine (Compound 8); MS (ESI), Calculated for $C_{12}H_{11}N_5S$: 257.07, Found (MH$^+$): 257.7;

2-[1,2,3]thiadiazol-4-yl-1H-benzimidazole-5-carboxamidine (Compound 9); MS (ESI), Calculated for $C_{10}H_8N_6S$: 244.05, Found (MH$^+$): 244.7;

2-(1H-imidazol-4-yl)-1H-benzimidazole-5-carboxamidine (Compound 10); MS (ESI), Calculated for $C_{11}H_{10}N_6$: 226.1, Found (MH$^+$): 226.6;

2-(2H-pyrazol-3-yl)-1H-benzimidazole-5-carboxamidine (Compound 11); MS (ESI), Calculated for $C_{12}H_{12}N_6$: 240.11, Found (MH$^+$): 241;

2-(2-pyridazin-3-yl)-1H-benzimidazole-5-carboxamidine (Compound 12); MS (ESI), Calculated for $C_{12}H_{10}N_6$: 238.1, Found (MH$^+$): 238.9;

2-[3-(1H-benzimidazol-2-yl)pyridin-2-yl]-1H-benzimidazole-5-carboxamidine (Compound 13); MS (ESI), Calculated for $C_{20}H_{15}N_7$: 353.14, Found (MH$^+$): 353.8;

2-(4,8-dihydroxyquinolin-2-yl)-1H-benzimidazole-5-carboxamidine (Compound 14); MS (BIOION), Calculated for $C_{17}H_{13}N_5O_2$: 319.11, Found (MH$^+$): 320.8;

2-(5-methyl-1H-imidazol-4-yl)-1H-benzimidazole-5-carboxamidine (Compound 15); MS (ESI), Calculated for $C_{12}H_{12}N_6$: 240.11, Found (MH$^+$): 240.7;

2-(5-methyl-1-benzyl-1H-imidazol-4-yl)-1H-benzimidazole-5-carboxamidine (Compound 16); MS (ESI), Calculated for $C_{19}H_{18}N_6$: 330.16, Found (MH$^+$): 338.6;

2-(1-benzyl-1H-imidazol-2-yl)-1H-benzimidazole-5-carboxamidine (Compound 17); MS (ESI), Calculated for $C_{18}H_{16}N_6$: 316.14, Found (MH$^+$): 316.9;

2-(6-hydroxypyridin-2-yl)-1H-benzimidazole-5-carboxamidine (Compound 18); MS (ESI), Calculated for $C_{13}H_{11}N_5O$: 253.1, Found (MH$^+$): 253.8;

2-(5-methyl-1-(2-phenylethyl)-1H-imidazol-4-yl)-1H-benzimidazole-5-carboxamidine (Compound 19); MS (ESI), Calculated for $C_{20}H_{20}N_6$: 344.17, Found (MH$^+$): 345;

2-(5-methyl-1-propyl-1H-imidazol-4-yl)-1H-benzimidazole-5-carboxamidine (Compound 20); MS (ESI), Calculated for $C_{15}H_{18}N_6$: 282.16, Found (MH$^+$): 283;

2-(5-methyl-1-phenyl-1H-pyrazol-3-yl)-1H-benzimidazole-5-carboxamidine (Compound 21); MS (BIOION), Calculated for $C_{18}H_{16}N_6$: 316.14, Found (MH$^+$): 317;

2-(5-methyl-2-pyridin-2-yl-2H-pyrazol-3-yl)-1H-benzimidazole-5-carboxamidine (Compound 22); MS (BIOION), Calculated for $C_{17}H_{15}N_7$: 317.14, Found (MH$^+$): 318.2;

6-(5-amidino-1H-benzimidazol-2-yl)pyridine-2-carboxylic acid (Compound 106); MS (ESI), Calculated for $C_{14}H_{11}N_5O_2$: 281.09, Found (MH$^+$): 281.9;

2-(5-methyl-1-pyridin-2-yl-1H-pyrazol-3-yl)-1H-benzimidazole-5-carboxamidine (Compound 23); MS (BIOION), Calculated for $C_{17}H_{15}N_7$: 317.14, Found (MH$^+$): 318;

2-(9H-β-carbolin-3-yl)-3H-benzoimidazole-5-carboxamidine (Compound 109): MS (bio ion) Calc.: 326.13; Found: 327.1;

2-(3-benzoylpyridin-2-yl)-3H-benzoimidazole-5-carboxamidine (Compound 110): MS (bio ion) Calc.: 341.3; Found: 340.5; and 2-{3-[2-(2-oxopyrrolidin-1-yl)ethoxy]pyridin-2-yl}-3H-benzoimidazole-5-carboxamidine (Compound 111): MS (bio ion) Calc.: 364.16 Found: 365.4.

Proceeding as in Example 10, but substituting suitable pyridine-2-carbonitrile derivatives for 5-butylpyridine-2-carboxylic acid, provided the following compounds of Formula I:

2-(5-nitropyridin-2-yl)-1H-benzimidazole-5-carboxamidine (Compound 24); $^1$H-NMR (300 Mhz, DMSO-d$_6$): 7.7 (d, 1H, J=8.2 Hz), 7.8 (d, 1H, J=8.2 Hz), 8.2 (s, 1H), 8.6 (d, 1H, J=8.7 Hz), 8.8 (dd, 1H, J=2.4 Hz, 8.7 Hz), 9.1 (s, 2H), 9.4 (s, 2H), 9.5 (d, 1H, J=2.4 Hz); MS (ESI), Calculated for $C_{13}H_{10}N_6O_2$: 282.3, Found (MH$^+$): 282.9;

2-(5-phenylpyridin-2-yl)-1H-benzimidazole-5-carboxamidine (Compound 25); $^1$H-NMR (300 Mhz, DMSO-d$_6$): 7.5 (m, 3H), 7.65 (d, 1H, J=9 Hz), 7.8 (d, 1H, J=9 Hz), 7.85 (m, 2H), 8.15 (s, 1H), 8.3 (d, 1H, J=3 Hz, 9 Hz) 8.4 (d, 1H, J=9 Hz), 8.9 (s, 2H); 9.1 (d, 1H, J=3 Hz), 9.3 (s, 2H; MS (ESI), Calculated for $C_{19}H_{15}N_5$: 313.4, Found (MH$^+$): 313.9;

2-(4-methylpyridin-2-yl)-1H-benzimidazole-5-carboxamidine (Compound 26); $^1$H-NMR (300 Mhz, DMSO-d$_6$): 2.5 (s, 3H), 7.5 (D, 1H, J=5 Hz), 7.7 (m, 2H), 8.2 (s, 1H), 8.4 (S, 1H), 8.7 (d, 1H, J=5 Hz), 9.3 (s, 2H), 9.5 (s, 2H); MS (ESI), Calculated for $C_{14}H_{13}N_5$: 251.3, Found (MH$^+$): 251.9; and 2-(1-butyl-1H-imidazol-2-yl)-1H-benzimidazole-5-carboxamidine (Compound 27); MS (ESI), Calculated for $C_{15}H_{18}N_6$: 282.16, Found (MH$^+$): 282.9.

Proceeding as in Example 10, but substituting suitable N-substituted benzamidine derivatives for 3,4-diaminobenzamidine hydrochloride, provided the following compounds of Formula I:

2-(5-butylpyridin-2-yl)-3-methyl-3H-benzimidazole-5-carboxamidine (Compound 28); $^1$H-NMR (300 Mhz, DMSO-d$_6$): 0.9 (t, 3H), 1.3 (m, 2H), 1.5 (m, 2H), 2.7 (t, 2H), 4.2 (s, 3H), 7.6 (d, 1H), 7.9 (m, 2H), 8.3 (m, 2H), 8.7 (s, 1H), 9.0 (s, 2H), 9.3 (s, 2H), Calculated for $C_{18}H_{21}N_5$: 307.4, Found (MH$^+$): 307.9; and 2-(5-butylpyridin-2-yl)-1-methyl-1H-benzimidazole-5-carboxamidine (Compound 29) $^1$H-NMR (300 Mhz, DMSO-d$_6$): 0.9 (t, 3H), 1.3 (m, 2H), 1.6 (m, 2H), 2.7 (t, 2H), 4.2 (s, 3H), 7.9 (m, 3H), 8.2 (d, 2H), 8.7 (s, 1H) 9.2 (bs, 4H; MS (ESI), Calculated for $C_{18}H_{21}N_5$: 307.4, Found (MH$^+$): 307.9;

Example 11

2-(5-Propoxypyridin-2-yl]-1H-benzimidazole-5-carboxamidine (Compound 30), a Compound of Formula I in which A Together with B Comprises 5-amidino-1H-benzimidazol-2-yl and C Comprises 5-propoxypyridin-2-yl A mixture comprising 5-propoxypyridine-2-carboxyaldehyde (0.19 g, 1.15 mmol), 3,4- diaminobenzamidine hydrochloride (0.21 g, 1.15 mmol) and nitrobenzene (2 mL) was heated at 150° C. for 15 hours, cooled and then diluted with 1:1 acetonitrile/ether (50 mL) to give a precipitate. The precipitate was isolated by filtration and purified by HPLC to provide 2-(5-propyloxypyridin-2-yl]-1H-benzimidazole-5-carboxamidine. $^1$H-NMR (300 Mhz, CD$_3$OD): 1.1 (t, 3H), 2.0 (m, 2H), 4.5 (t, 2H), 7.75 (m, 1H), 7.86 (m, 2H), 8.1 (m, 1H), 8.35 (m, 1H); 8.55 (m, 1H); MS (ESI), Calculated for C$_{16}$H$_{17}$N$_5$O: 295.3, Found (MH$^+$): 295.9.

Example 12

Ethyl 4-(5-amidino-1H-benzimidazol-2-yl)-5-methylimidazol-1-ylacetate (Compound 31), a Compound of Formula I in which A Together with B Comprises 5-amidino-1H-benzimidazol-2-yl and C Comprises 1-ethoxycarbonylmethyl-5-methyl-1H-imidazol-4-yl A mixture comprising ethyl 4-formyl-5-methylimidazol-1-ylacetate (0.3 g, 1.5 mmol), 4-diaminobenzamidine hydrochloride (0.3 g, 1.7 mmol), benzoquinone (0.18 g, 1.7 mmol) and ethanol (10 mL) was heated at reflux for 2.5 hours, cooled and concentrated under reduced pressure. The residue was dissolved in methanol (2 mL) and the solution was added to stirring acetonitrile (100 mL) to give a precipitate. The precipitate was isolated by filtration to provide ethyl 4-(5-amidino-1H-benzimidazol-2-yl)-5-methylimidazol-1-ylacetate (0.46 g, 1.4 mmol). $^1$H-NMR (300 Mhz, DMSO-d$_6$): 1.2 (t, 3H), 2.6 (s, 3H), 4.2 (q, 2H), 5.1 (s, 2H), 7.7 (m, 2H), 7.9 (s, 1H), 8.1 (s, 1H), 9.2 (s, 2H), 9.4 (s, 2H); MS (BIOION), Calculated for C$_{16}$H$_{18}$N$_6$O$_2$: 326.4, Found (MH$^+$): 327.3.

Proceeding as in Example 12, but substituting different starting materials, the following compounds of Formula I were provided:

- 2-(1-phenyl-1H-imidazol-2-yl)-1H-benzimidazole-5-carboxamidine (Compound 32); MS (ESI), Calculated for C$_{17}$H$_{14}$N$_6$: 302.13, Found (MH$^+$): 302.9;
- ethyl 2-(5-amidino-1H-benzimidazol-2-yl)imidazol-1-ylacetate (Compound 33); MS (ESI), Calculated for C$_{15}$H$_{16}$N$_6$O$_2$: 312.13, Found (MH$^+$): 312.9;
- tert-butyl 4-(5-amidino-1H-benzimidazol-2-yl)-5-methylimidazol-1-ylacetate (Compound 34); MS (ESI), Calculated for C$_{18}$H$_{22}$N$_6$O$_2$: 354.18, Found (MH$^+$): 355;
- 3-methyl-2-(5-methyl-1H-imidazol-4-yl)-3H-benzimidazole-5-carboxamidine (Compound 35); MS (ESI), Calculated for C$_{13}$H$_{14}$N$_6$: 254.13, Found (MH$^+$): 254.9;
- 2-{1-[3-(1,3-dioxo-1,3-dihydroisoindol-2-yl)propyl]-5-methyl-1H-imidazol-4-yl}-1H-benzimidazole-5-carboxamidine (Compound 36); MS (ESI), Calculated for C$_{23}$H$_{21}$N$_7$O$_2$: 427.18, Found (MH$^+$): 428;
- N-cyano-2-pyridin-2-yl-1H-benzimidazole-5-carboxamidine (Compound 37); MS (ESI), Calculated for C$_{14}$H$_{10}$N$_6$: 262.1, Found (MH$^+$): 262.7;
- ethyl 4-[2-(5-amidino-1H-benzimidazol-2-yl)imidazol-1-yl]butyric acid (Compound 38); MS (ESI), Calculated for C$_{17}$H$_{20}$N$_6$O$_2$: 340.16, Found (MH$^+$): 340.9;
- 2-{1-[4-(1,3-dioxo-1,3-dihydroisoindol-2-yl)butyl]-1H-imidazol-2-yl}-1H-benzimidazole-5-carboxamidine (Compound 39); MS (ESI), Calculated for C$_{23}$H$_{21}$N$_7$O$_2$: 427.18, Found (MH$^+$): 428.1;
- 2-(8-hydroxyquinolin-2-yl)-1H-benzimidazole-5-carboxamidine (Compound 42); MS (BIOION), Calculated for C$_{17}$H$_{13}$N$_5$O: 303.11, Found (MH$^+$): 304.2;
- N-hydroxy-2-(1H-imidazol-2-yl)-3H-benzoimidazole-5-carboxamidine (Compound 113); $^1$H NMR (MEOH-d$_4$) δ 8.21 (S, 1H), 7.91 (d, 1H, J=8 Hz), 7.82 (S, 2H), 7.73 (d, 1H, J=8 Hz) MS (bio ion); Calc: 242.1; Found: 243.2;
- N-methoxy-2-pyridin-2-yl-3H-benzoimidazole-5-carboxamidine (Compound 114); $^1$H NMR (DMSO-d$_6$) δ 8.85 (d, 1H, J=3 Hz), 8.60 (d, 1H, J=8 Hz), 8.20–8.10 (m, 2H), 7.90–7.65 (M, 3H), 3.90 (S, 3H), MS (ES); Calc.: 267.11; Found: 267.9;
- 3-(2-aminoethyl)-N-hydroxy-2-pyridin-2-yl-3H-benzoimidazole-5-carboxamidine (Compound 115); $^1$H NMR (DMSO-d$_6$) δ 8.84 (d, 1H, J=3 Hz), 8.50–8.35 (M, 2H), 8.10 (M, 1H), 7.95 (M, 1H), 7.70–7.60 (M, 2H), 5.10 (t, 2H, J=6 Hz), 3.50 (M, 2H). MS (ES); Calc.: 296.14; Found: 297.0;
- 2-(3-chloro-5-trifluoromethylpyridin-2-yl)-3H-benzoimidazole-5-carboxamidine (Compound 116); MS (bio ion) Calc.: 339.05; Found: 340.0;
- 2-(8-benzyloxyquinolin-2-yl)-3H-benzoimidazole-5-carboxamidine (Compound 117); MS (bio ion) Calc.: 393.16; Found: 394.0;
- 2-(1H-imidazol-2-yl)-3H-benzoimidazole-5-carboxamidine (Compound 118); $^1$H NMR (DMSO-d$_6$) δ 7.82 (dd, 1H, J=8.4, 1.5), 7.83 (S, 2H), 7.91 (d, 1H, J=8.4 Hz), 8.34 (d, 1H, J=1.5 Hz), 9.32 (S, 2H), 9.55 (S, 2H), MS (bio ion) Calc.: 226.10; Found: 227.4; and
- 2-{1-[2-(1,3-dioxo-1,3-dihydroisoindol-2-yl)ethyl]-1H-imidazol-2-yl}-3H-benzoimidazole-5-carboxamidine (Compound 119); $^1$H NMR (DMSO-d6), δ 4.09 (M, 2H), 4.95 (M, 2H), 7.27 (d, 1H, J=3.1 Hz), 7.57 (d, 1H, J=3.1), 7.60 (S, 1H), 7.63 (M, 5H), 7.99 (br, S, 1H), 9.08 (S, 2H), 9.33 (S, 2H). MS (ES) Calc.: 399.14; Found 400.1.

Example 13

Methyl 6-(5-amidino-1H-benzimidazol-2-yl)pyridine-4-carboxylate (Compound 44), a Compound of Formula I in which A Together with B Comprises 5-amidino-1H-benzimidazol-2-yl and C Comprises 4-methoxcarbonylpyridin-2-yl A mixture comprising 3,4-diaminobenzamidine hydrochloride (1.16 g, 6.2 mmol), methyl 2-(C-ethoxyiminomethyl)pyridine-4-carboxylate (1.8 g, 7.4 mmol) and anhydrous methanol (6 mL) was stirred for 20 hours. The mixture was concentrated and the residue was trituated with hot methanol (5 mL). The solid was isolated and dried to provide methyl 2-(5-amidino-1H-benzimidazol-2-yl)pyridine-4-carboxylate (1.8 g, 5.1 mmol); Calculated for C$_{15}$H$_{13}$N$_5$O$_2$: 295.3, Found (MH$^+$): 295.7.

Example 14

66-(5-Amidino-1H-benzimidazol-2-yl)pyridine-3-carboxylic Acid (Compound 45), a Compound of Formula I in which A Together with B Comprises 5-amidino-1H-benzimidazol-2-yl and C Comprises 3-carboxypyridin-2-yl A mixture comprising ethyl 6-(5-amidino-1H-benzimidazol-2-yl)pyridine-3-carboxylate (1.7 g, 5.7 mmol) and 3N hydrochloric acid (60 mL) was heated at reflux for 24 hours. The mixture was cooled, concentrated to one quarter volume and poured into stirring acetonitrile (200 mL) to give a precipitate. The precipitate was filtered and dried under vacuum to provide 6-(5-amidino-1H-benzimidazol-2-yl)pyridine-3-carboxylic acid (1.4 g, 5.0 mmol). $^1$H-NMR (300 Mhz, DMSO-d$_6$): 7.7 (m, 2H), 8.2 (s, 1H), 8.5 (m, 2H), 9.2 (s, 1H), 9.3 (s, 2H) 9.5 (s, 2H); MS (ESI), Calculated for $C_{14}H_{11}N_5O_2$: 281.3, Found (MH$^+$): 281.9.

Proceeding as in Example 14, but substituting different starting materials, the following compounds of Formula I were provided:

4-[2-(5-amidino-1H-benzimidazol-2-yl)imidazol-1-yl] butyric acid (Compound 47); MS (ESI), Calculated for $C_{15}H_{16}N_6O_2$: 312.13, Found (MH$^+$): 312.9; and 2-(5-amidino-1H-benzimidazol-2-yl)pyridine-4-carboxylic acid (Compound 43), $^1$H-NMR (300 Mhz, DMSO-d$_6$): 7.7 (m, 2H), 8.0 (d, 1H, J=5 Hz), 8.2 (s, 1H), 8.7 (s, 1H), 9.0 (d, 1H, J=5 Hz), 9.2 (s, 2H), 9.4 (s, 2H); MS (BIOION), Calculated for $C_{14}H_{13}N_5O_2Cl_2$: 281.3, Found (MH$^+$): 282.3.

Example 15

2-(5-Amidino-1H-benzimidazol-2-yl)-N-benzylpyridine-4-carboxamide (Compound 48), a Compound of Formula I in which A Together with B Comprises 5-amidino-1H-benzimidazol-2-yl and C Comprises 4-benzylcarbamoylpyridin-2-yl A mixture comprising 2-(6-amidino-1H-benzimidazol-2-yl)pyridine-4-carboxylic acid (0.02 g, 0.06 mmol), HOBT (0.008 g, 0.07 mmol), PyBOP (0.032 g, 0.07 mmol), DMF (0.5 mL) and N-methylmorpholine (0.013 mL, 0.12 mmol) was shaken for 10 minutes and then benzyl amine (13 μL, 0.12 mmol) was added. The mixture was shaken for approximately 12 hours and combined with a mixture comprising ether and acetonitrile (5 mL) to give a precipitate. The precipitate was isolated by filtration and purified by HPLC to provide 6-(5-amidino-1H-benzimidazol-2-yl)-N-benzylpyridine-4-carboxamide (10 mg, 0.02 mmol); $^1$H-NMR (300 Mhz, DMSO-d$_6$): 4.5 (d, 2H, J=5.5 Hz), 7.3 (m, 5H), 7.7 (m, 2H), 8.0 (dd, 1H), 8.2 (bs, 1H), 8.8 (s, 1H), 8.9 (m, 3H), 9.3 (s, 2H), 9.6 (t, 1H, J=1.5 Hz); MS (ESI), Calculated for $C_{21}H_{18}N_6O$: 370.4, Found (MH$^+$): 371.1.

Proceeding as in Example 15, but substituting different amines, the following compounds of Formula I were provided:

2-(4-morpholin-4-ylcarbonylpyridin-2-yl)-1H-benzimidazole-5-carboxamidine Compound 49); MS (ESI), Calculated for $C_{18}H_{18}N_6O_2$: 350.4, Found (MH$^+$): 351.1;

6-(5-amidino-1H-benzimidazol-2-yl)-N-[2-(4-methoxyphenyl)ethyl]pyridine-4-carboxamide (Compound 50); MS (ESI), Calculated for $C_{23}H_{22}N_6O_2$: 414.5, Found (MH$^+$): 414.9;

6-(5-amidino-1H-benzimidazol-2-yl)-N-(2-methoxyethyl)pyridine-4-carboxamide (Compound 51); MS (ESI), Calculated for $C_{17}H_{18}N_6O_2$: 338.4, Found (MH$^+$): 338.9;

6-(5-amidino-1H-benzimidazol-2-yl)-N-(3-methylbutyl)pyridine-4-carboxamide (Compound 52); MS (ESI), Calculated for $C_{19}H_{22}N_6O$: 350.4, Found (MH$^+$): 351.0;

(S)-2-[2-(5-amidino-1H-benzimidazol-2-yl)pyridin-4-ylcarbonylamino]-4-carbamoylbutyric acid (Compound 53); MS (ESI), Calculated for $C_{19}H_{19}N_7O_4$: 409.4, Found (MH$^+$): 410.0;

6(5-amidino-1H-benzimidazol-2-yl)-N-benzylpyridine-3-carboxamide (Compound 54); $^1$H-NMR (300 Mhz, DMSO-d$_6$): 4.5 (d, 2H, J=6 Hz), 7.3 (m, 5H), 7.7 (d, 1H, J=8.3 Hz), 7.8 (d, 1H, J=8.3 Hz), 8.2 (s, 1H) 8.5 (m, 2H), 9.0 (s, 2H), 9.3 (s, 1H), 9.4 (s, 2H), 9.5 (t, 1H, J=6 Hz); MS (ESI), Calculated for $C_{21}H_8N_6O$: 370.4, Found (MH$^+$): 371.1;

6-(5-amidino-1H-benzimidazol-2-yl)-N-(2-methoxyethyl)pyridine-5-carboxamide (Compound 55); MS (ESI), Calculated for $C_{17}H_{18}N_6O_2$: 338.4, Found (MH$^+$): 339.1;

2-(5-morpholin-4-ylcarbonylpyridin-2-yl)-1H-benzimidazole-5-carboxamidine (Compound 56); MS (ESI), Calculated for $C_{18}H_{18}N_6O_2$: 350.4, Found (MH$^+$): 351.1;

6-(5-amidino-1H-benzimidazol-2-yl)-N-[2-(3-bromo-4-methoxyphenyl)ethyl]pyridine-5-carboxamide (Compound 57); MS (ESI), Calculated for $C_{23}H_{21}N_6BrO_2$: 493.4, Found (MH$^+$): 495.1;

6-(5-amidino-1H-benzimidazol-2-yl)-N-(3-methylbutyl)pyridine-5-carboxamide (Compound 58); MS (ESI), Calculated for $C_{19}H_{22}N_6O$: 350.4, Found (MH$^+$): 351.2;

2S-[6-(5-amidino-1H-benzimidazol-2-yl)pyridin-3-ylcarbonylamino]-3R-hydroxybutyric acid (Compound 59); MS (ESI), Calculated for $C_{18}H_{18}N_6O_4$: 382.4, Found (MH$^+$): 383.6;

6-(5-amidino-1H-benzimidazol-2-yl)-N-(2-phenylethyl)pyridine-5-carboxamide (Compound 60); MS (ESI), Calculated for $C_{22}H_{20}N_6O$: 384.4, Found (MH$^+$): 385.0;

6-(5-amidino-1H-benzimidazol-2-yl)-N-(3-phenylpropyl)pyridine-5-carboxamide (Compound 61); MS (ESI), Calculated for $C_{23}H_{22}N_6O$: 398.5, Found (MH$^+$): 399.0;

6-(5-amidino-1H-benzimidazol-2-yl)-N-(2-benzo[1,3]dioxol-4-ylethyl)pyridine-5-carboxamide (Compound 62); MS (ESI), Calculated for $C_{23}H_{20}N_6O_3$: 428.5, Found (MH$^+$): 429.0;

6-(5-amidino-1H-benzimidazol-2-yl)-N-[2-(4-methoxyphenoxy)ethyl]pyridine-5-carboxamide (Compound 63); MS (ESI), Calculated for $C_{21}H_{22}N_6O_3$: 406.4, Found (MH$^+$): 431.0;

6-(5-amidino-1H-benzimidazol-2-yl)-N-(2-naphth-1-ylethylcarbamoyl)pyridine-5-carboxamide (Compound 64); MS (ESI), Calculated for $C_{26}H_{22}N_6O$: 434.5, Found (MH$^+$): 435.0;

(S)-2-[6-(5-amidino-1H-benzimidazol-2-yl)pyridin-3-ylcarbonylamino]-3-phenylpropionic acid (Compound 65); MS (ESI), Calculated for $C_{23}H_{19}N_6O_3$: 428.4, Found (MH$^+$): 429.0;

6-(5-amidino-1H-benzimidazol-2-yl)-N-[2-(4-methoxyphenyl)ethyl]pyridine-5-carboxamide (Compound 66); MS (ESI), Calculated for $C_{23}H_{22}N_6O_2$: 414.5, Found (MH$^+$): 414.9;

(S)-2-[6-(5-amidino-1H-benzimidazol-2-yl)pyridin-3-ylcarbonylamino]-3-(4-hydroxyphenyl)propionic acid (Compound 67); MS (ESI), Calculated for $C_{23}H_{22}N_6O_4$: 444.5, Found (MH$^+$): 444.9;

6-(5-amidino-1H-benzimidazol-2-yl)-N-[2-(3-methoxyphenyl)ethyl]pyridine-5-carboxamide (Compound 68); MS (ESI), Calculated for $C_{23}H_{22}N_6O_2$: 414.5, Found (MH$^+$): 414.9;

6-(5-amidino-1H-benzimidazol-2-yl)-N-(2-morpholin-4-ylethyl)pyridine-5-carboxamide (Compound 69; $K_i$=0.04 μM); MS (ESI), Calculated for $C_{20}H_{23}N_7O_2$: 393.5, Found (MH$^+$): 394.0;

4-(5-amidino-1H-benzimidazol-2-yl)-5-methylimidazol-1-yl-N-[2-(4-methoxyphenyl)ethyl]acetamide (Compound 70); $^1$H-NMR (300 Mhz, DMSO-d$_6$): 2.7 (s, 3H), 2.8 (t, 2H, J=7.2 Hz), 3.5 (m, 2H), 4.9 (s, 2H), 7.0 (d, 2H, J=8.2 Hz), 7.3 (d, 2H, J=8.2 Hz), 7.8 (m, 2H), 8.0 (s, 1H), 8.4 (s, 1H), 8.5 (t, 1H), 9.1 (s, 2H), 9.5 (s, 2H), MS (ESI), calculated for $C_{23}H_{25}N_7O_2$: 431.5, Found (MH$^+$): 432.1;

4-(5-amidino-1H-benzimidazol-2-yl)-5-methylimidazol-1-yl-N-(3-methylbutyl)acetamide (Compound 71); MS (ESI), Calculated for $C_{19}H_{25}N_7O$: 367.5, Found (MH$^+$): 368;

4-(5-amidino-1H-benzimidazol-2-yl)-5-methylimidazol-1-yl-N-benzylacetamide (Compound 72); MS (ESI), Calculated for $C_{21}H_{21}N_7O$: 387.5, Found (MH$^+$): 388.0;

methyl 2-{2-[2-(5-amidino-1H-benzimidazol-2-yl)imidazol-1-ylacetylamino]ethoxy}benzoate (Compound 73); MS (ESI), Calculated for $C_{23}H_{23}N_7O_4$: 461.48, Found (MH$^+$): 462.2;

2-[4-(5-amidino-1H-benzimidazol-2-yl)-5-methylimidazol-1-yl]acetylaminoacetic acid (Compound 74); MS (ESI), Calculated for $C_{16}H_{17}N_7O_3$: 355.4, Found (MH$^+$): 356.2;

2-{2-[4-(5-amidino-1H-benzimidazol-2-yl)-5-methylimidazol-1-yl]acetylamino}propionic acid (Compound 75); MS (ESI), Calculated for $C_{16}H_{17}N_7O_3$: 369.4, Found (MH$^+$): 370.2;

1-[4-(5-amidino-1H-benzimidazol-2-yl)-5-methylimidazol-1-yl]acetylpyrrolidine-2-carboxylic acid (Compound 76); MS (BIOION), Calculated for $C_{19}H_{21}N_7O_3$: 395.4, Found (MH$^+$): 386.1;

2-{2-[4-(5-amidino-1H-benzimidazol-2-yl)-5-methylimidazol-1-yl]acetylamino}succinic acid (Compound 77); MS (BIOION), Calculated for $C_{18}H_{19}N_7O_5$: 413.4, Found (MH$^+$): 415.1;

2-{2-[4-(5-amidino-1H-benzimidazol-2-yl)-5-methylimidazol-1-yl]acetylamino}-6-aminohexanoic acid (Compound 78); MS (BIOION), Calculated for $C_{20}H_{26}N_8O_3$: 426.5, Found (MH$^+$): 427.7;

2-{2-[4-(5-amidino-1H-benzimidazol-2-yl)-5-methylimidazol-1-yl]acetylamino}-3-methylbutyric acid (Compound 79); MS (BIOION), Calculated for $C_{19}H_{23}N_7O_3$: 397.4, Found (MH$^+$): 397.3;

2-[2-[4-(5-amidino-1H-benzimidazol-2-yl)-5-methylimidazol-1-yl]acetylamino}-3-hydroxypropionic acid (Compound 80); MS (BIOION), Calculated for $C_{11}H_{15}NO_3$: 385.4, Found (MH$^+$): 386.1;

2-{2-[4-(5-amidino-1H-benzimidazol-2-yl)-5-methylimidazol-1-yl]acetylamino}-4-methylpentanoic acid (Compound 81); MS (BIOION), Calculated for $C_{20}H_{25}N_7O_3$: 411.5, Found (MH$^+$): 411.7;

2-{2-[4-(5-amidino-1H-benzimidazol-2-yl)-5-methylimidazol-1-yl]acetylamino}-3-phenylpropionic acid (Compound 82); MS (BIOION), Calculated for $C_{23}H_{23}N_7O_3$: 445.5, Found (MH$^+$): 446.1;

2-{2-[4-(5-amidino-1H-benzimidazol-2-yl)-5-methylimidazol-1-yl]acetylamino}succinamic acid (Compound 83); MS (BIOION), Calculated for $C_{18}H_{21}N_8O_4$: 412.4, Found (MH$^+$): 413.4;

6-(5-amidino-1H-benzimidazol-2-yl)-N-[2-(3,4-dimethoxyphenyl)ethyl]pyridine-5-carboxamide (Compound 84); MS (ESI), Calculated for $C_{24}H_{24}N_6O_3$: 444.19, Found (MH$^+$): 445.1;

6-(5-amidino-1H-benzimidazol-2-yl)-N-[2-(4-hydroxyphenyl)ethyl]pyridine-5-carboxamide (Compound 85); MS (ESI), Calculated for $C_{22}H_{20}N_6O_2$: 400.16, Found (MH$^+$): 401;

6-(5-amidino-1H-benzimidazol-2-yl)-N-[2-(4-methylphenyl)ethyl]pyridine-5-carboxamide (Compound 86); MS (ESI), Calculated for $C_{23}H_{22}N_6O$: 398.19, Found (MH$^+$): 399;

6-(5-amidino-1H-benzimidazol-2-yl)-N-[2-(4-chlorophenyl)ethyl]pyridine-5-carboxamide (Compound 87); MS (ESI), Calculated for $C_{22}H_{19}ClN_6O$: 418.13, Found (MH$^+$): 419;

6-(5-amidino-1H-benzimidazol-2-yl)-N-[2-(3,4-dichlorophenyl)ethyl]pyridine-5-carboxamide (Compound 88); MS (ESI), Calculated for $C_{22}H_{18}Cl_2N_6O$: 452.09, Found (MH$^+$): 453.1;

2(5-amidino-1H-benzimidazol-2-yl)imidazol-1-yl-N-(2-p-tolylethyl)acetamide (Compound 89); MS (ESI), Calculated for $C_{22}H_{23}N_7O$: 401.2, Found (MH$^+$): 402.2;

2-(5-amidino-1H-benzimidazol-2-yl)imidazol-1-yl-N-[2-(4-chlorophenyl)ethyl]acetamide (Compound 90); MS (ESI), Calculated for $C_{21}H_{20}ClN_7O$: 421.14, Found (MH$^+$): 422.1;

2-(5-amidino-1H-benzimidazol-2-yl)imidazol-1-yl-N-[2-(3,4-dimethoxy)ethyl]acetamide (Compound 91); MS (ESI), Calculated for $C_{23}H_{25}N_7O_2$: 447.2, Found (MH$^+$): 447.4;

4-(5-amidino-1H-benzimidazol-2-yl)-5-methylimidazol-1-yl-N-[2-(3,4-dimethoxyphenyl)ethyl]acetamide (Compound 92); MS (ESI), Calculated for $C_{25}H_{29}N_7O_3$: 475.23, Found (MH$^+$): 476.1;

methyl 2-{2-[4-(5-amidino-1H-benzimidazol-2-yl)-5-methylimidazo-1-ylcarbonylamino]ethoxy}benzoate (Compound 93); MS (ESI), Calculated for $C_{24}H_{25}N_7O_4$: 475.2, Found (MH$^+$): 476.1;

4-(5-amidino-1H-benzimidazol-2-yl)-5-methylimidazol-1-yl-N-(2-aminoethyl)acetamide (Compound 94); MS (ESI), Calculated for $C_{16}H_{20}N_8O$: 340.18, Found (MH$^+$): 341;

2-(5-amidino-1H-benzimidazol-2-yl)imidazol-1-yl-N-[2-(4-hydroxyphenyl)ethyl]acetamide (Compound 95); MS (ESI), Calculated for $C_{21}H_{21}N_7O_2$: 403.18, Found (MH$^+$): 404.2;

2-(5-amidino-1H-benzimidazol-2-yl)imidazol-1-yl-N-(2-naphth-1-ylethyl)acetamide (Compound 96); MS (ESI), Calculated for $C_{25}H_{23}N_7O$: 437.2, Found (MH$^+$): 438.2;

2-(5-amidino-1H-benzimidazol-2-yl)imidazol-1-yl-N-(4-methoxybenzyl)acetamide (Compound 97); MS (ESI), Calculated for $C_{21}H_{21}N_7O_2$: 403.18, Found (MH$^+$): 404.1;

2-[1-(3-morpholin-4-ylcarbonylpropyl)-1H-imidazol-2-yl]-1H-benzimidazole-5-carboxamidine (Compound 98); MS (ESI), Calculated for $C_{19}H_{23}N_7O_2$: 381.19, Found (MH$^+$): 382.1;

4-[2-(5-amidino-1H-benzimidazol-2-yl)imidazol-1-yl]-N-pyridin-3-ylmethylbutyramide (Compound 99); MS (ESI), Calculated for $C_{21}H_{22}N_8O$: 402.19, Found (MH$^+$): 403.1;

4-[2-(5-amidino-1H-benzimidazol-2-yl)imidazol-1-yl]-N-[2-(4-chlorophenyl)ethyl]butyramide (Compound 100); MS (ESI), Calculated for $C_{23}H_{24}ClN_7O$: 449.17, Found (MH$^+$): 450.1;

4-[2-(5-amidino-1H-benzimidazol-2-yl)imidazol-1-yl]-N-[2-(3,4-dimethoxyphenyl)ethyl]butyramide (Compound 101); MS (ESI), Calculated for $C_{25}H_{29}N_7O_3$: 475.23, Found (MH$^+$): 476.3;

2-[1-(3-piperazin-1-ylcarbonylpropyl)-1H-imidazol-2-yl]-1H-benzimidazole-5-carboxamidine (Compound 102); MS (ESI), Calculated for $C_{19}H_{24}N_8O$: 380.21, Found (MH$^+$): 381.3; and 2-{1-[4-(4-benzylpiperazin-1-yl)-4-oxobutyl]-1H-imidazol-2-yl}-3H-benzoimidazole-5-carboxamidine (Compound 112); $^1$H NMR (DMSO-d6) δ 9.47 (S, 2H), 9.22 (S, 2H), 8.26 (S, 1H), 7.90–7.70 (M, 3H), 7.65–7.50 (M, 3H), 7.47–7.30 (M, 3H), 4.80 (t, 2H, J=6 Hz), 4.30 (M, 3H), 3.95 (M, 1H), 3.50 (M, 1H), 3.25–2.70 (M, 3H), 2.50–2.30 (M, 4H), 2.10 (M, 2H). MS (ES); Calc: 470.25; Found: 471.2.

Example 16

N-Hydroxy-2-pyridin-2-yl-1H-benzimidazole-5-carboxamidine (Compound 103), a Compound of Formula I in which A Together with B Comprises N-hydroxyamidino-1H-benzimidazol-2-yl and C Comprises pyridin-2-yl A mixture comprising 4-amino-3-nitrobenzonitrile (5 g, 0.031 mmol) and palladium on carbon (500 mg, 10 wt %) and ethyl acetate (150 mL) in a Parr flask was hydrogenated for 60 minutes (45–50 psi), filtered over celite and concentrated to dryness to provide 3,4-diaminobenzonitrile (4.09 g, 0.031 mol) as a white solid; PB-CI/MS: 134=(MH$^+$); $^1$H-NMR (300 Mhz, DMSO-d$_6$): 4.81 (bs, 2H), 5.39 (bs, 2H), 6.494 (d, 1H), 6.703 (s, 1H), 6.723 (d, 1H).

A mixture comprising 2-pyridinecarboxaldehyde (212 mg, 1.98 mmol, 1 eq), 3,4-diaminobenzonitrile (263 mg, 1.98 mmol, 1 eq) and ethanol (20 mL) was stirred at ambient temperature under nitrogen for 5 to 10 minutes and then 1,4-benzoquinone (233 mg, 2.16 mmol, 1.2 eq) was added. The mixture was heated at reflux for 3 hours and then concentrated. The residue was partitioned between ethyl acetate and saturated sodium bicarbonate. The organic layer was separated, dried (MgSO$_4$), filtered and concentrating to dryness to provide 2-pyridin-2-yl-1H-benzimidazole-5-carbonitrile (348 mg, 1.58 mmol) as an off white solid; ESI LC/MS: 261.9=(MH$^+$+CH$_3$CN); $^1$H-NMR (300 Mhz, DMSO-d$_6$): 7.65–7.755 (m, 2H), 7.769 (d, 1H), 8.060 (t, 1H), 8.163 (s, 1H), 8.395 (d, 1H), 8.772 (d, 1H).

A mixture comprising 2-pyridin-2-yl-1H-benzimidazole-5-carbonitrile (110 g, 0.5 mmol), hydroxylamine hydrochloride (38.2 mg, 0.55 mmol), potassium carbonate (104 mg, 0.75 mmol) and methanol (10 mL) was heated at reflux for 2.5 hours and then concentrated to dryness. The residue was taken up and purified by preparative reverse phase HPLC. The combined pure fractions were lyophilized to provide N-hydroxy-2-pyridin-2-yl-1H-benzimidazole-5-carboxamidine (40 mg, 0.23 mmol); $^1$H-NMR (300 Mhz, DMSO-d$_6$): 7.53–7.57 (m, 2H), 7.80 (d, 1H), 8.01–8.04 (m, 2H), 8.32 (d, 1H), 8.75 (d, 1H), 9.20 (b, 2H); MS (ESI), Calculated for $C_{13}H_{11}N_5O$: 253.1, Found (MH$^+$): 253.7.

Proceeding as in Example 16, but substituting different starting materials, provided 6-fluoro-N-hydroxy-2-pyridin-2-yl-1H-benzimidazole-5-carboxamidine trifluoroacetate (Compound 104); MS (ESI), Calculated for $C_{13}H_{10}FN_5O$: 271.09, Found (MH$^+$): 271.9; $^1$H-NMR (300 Mhz, DMSO-d$_6$): 7.54–7.58 (m, 2H), 7.90 (d, 1H), 8.03 (m, 1H), 8.31 (d, 1H), 8.76 (d, 1H), 9.20 (b, 2H).

Example 17

6-Fluoro-2-pyridin-2-yl-1H-benzimidazole-5-carboxamidine (Compound 105), a Compound of Formula I in which A Together with B Comprises 5-amidino-1H-benzimidazol-2-yl and C Comprises 6-fluoropyridin-2-yl A mixture comprising 6-fluoro-N-hydroxy-2-pyridin-2-yl-1H-benzimidazole-5-carboxamidine trifluoroacetate (108 mg, 0.4 mmol), Zn (55 mg, 1.2 mmol) and acetic acid (5 mL) was heated at reflux under nitrogen for 2 hours. The mixture was filtered and concentrated to dryness. The residue was taken up and purified by preparative reverse phase HPLC. The combined pure fractions were lyophilized to provide 6-fluoro-2-pyridin-2-yl-1H-benzimidazole-5-carboxamidine; MS (ESI), Calculated for $C_{13}H_{10}FN_5$: 255.09, Found (MH$^+$): 255.9; $^1$H-NMR (300 Mhz, DMSO-d$_6$): 7.64–7.69 (m, 2H), 7.97 (d, 1H), 8.08 (m, 1H), 8.42 (d, 1H), 8.78 (d, 1H), 8.48 (d, 4H).

Example 18

2-pyrimidin-2-yl-1H-benzimidazole-5-carboxamidine (Compound 108), a Compound of Formula I in which A Together with B Comprises 5-amidino-1H-benzimidazol-2-yl and C Comprises 2-pyrimidin-2-yl A mixture comprising 3,4-diaminoamidine hydrochloride (0.29 g, 1.6 mmol), 2-(C-ethoxyiminomethyl)pyrimidine hydrochloride (0.29 g, 1.6 mmol) and anhydrous methanol (3 mL) was heated at reflux for 5 hours and concentrated. The residue (20 mg) was purified by reverse phase HPLC to provide 2-pyrimidin-2-yl-1H-benzimidazole-5-carboxamidine (8.6 mg, 0.02 mmol). MS (ESI), Calculated for $C_{12}H_{10}N_6$: 238.25; found (MH+): 238.7.

Example 19

In Vitro Enzyme Inhibitor Assay

The following represents an assay for determining the Factor Xa inhibitory activity of compounds of Formula I.

Mixtures of human Factor Xa (0.5–5 nM) and test compound (varying concentrations) in assay medium (comprising: Tris, 50 mM (pH 8); NaCl, 1M; CaCl$_2$, 5 mM; polyoxyethylenesorbitan monolaurate (Tween-20), 0.05%; DMSO, 10%; zinc chloride, 150 μM) were incubated for 1 hour at room temperature and then substrate, MesOC-Norleu-Gly-Arg-pNA, was added such that the final concentration of the substrate in the assay mixture was between 0.5 and 5 mM. Hydrolysis of the substrate was followed spectrophotometrically at (405 λ) for 5 minutes. Apparent inhibition constants (K$_i$) were calculated from the enzyme progress curves using standard mathematical models.

Proceeding as in Example 19 or by methods known to those of ordinary skill the following compounds of Formula I were tested for factor Xa inhibitory activity:

Compound 1, K$_i$=0.003 μM; Compound 16, K$_i$=0.008 μM; Compound 17, K$_i$=0.004 μM; Compound 20, K$_i$=0.007 μM; Compound 27, K$_i$=0.005 μM; Compound 33; K$_i$=0.005 μM; Compound 36, K$_i$=0.005 μM; Compound 39, K$_i$=0.006 μM; Compound 50, K$_i$=0.01 μM; Compound 57, K$_i$=0.002 μM; Compound 86, K$_i$=0.008 μM; Compound 88, K$_i$=0.006 μM; Compound 90, K$_i$=0.003 μM; Compound 95, K$_i$=0.006 μM; Compound 96, K$_i$=0.03 μM; Compound 98, K$_i$=0.002 μM; and Compound 100, K$_i$=0.006 μM.

Example 20

Ex vivo ACT Assay

Rabbits were sedated with Hypnorm® (fluanisone 10 mg/mL and phentanylcitrate 0.315 mg/mL; 0.05 mL/kg, i.m.). A catheter (Venflon®2, Ø 0.8/25 mm) was inserted into a marginal ear vein for administration of test compound. A second catheter (Venflon®2, Ø 1.0/32 mm) was inserted into the artery of the other ear for blood sampling. Test compounds were administered by i.v. bolus injection. Blood samples were collected (0.5 mL) prior to administration of test compounds and at various time points thereafter.

The activating clotting time (ACT), the amount of time for clot formation, was measured with a Medtronic Automated Coagulation Timer ACT II. An aliquot (200 μL) of the blood sample was added to each of two reaction chambers of a disposable two-channel test cartridge containing assay buffer (comprising: 0.75% kaolin as the activator and 0.0025M $CaCl_2$ in 0.1 mL HEPES buffer for non-citrated blood; or 2.2% kaolin and 0.05M $CaCl_2$ in 0.1 mL HEPES buffer for citrated blood). Clot formation was measured as a decrease in the downward motion of a plunger assembly contained by the test cartridge. The decrease in downward motion of the plunger was detected by a photo-optic system.

Proceeding as described in Example 20, compounds of the present Invention were assayed and found to increase ACT.

Example 20

In vitro ACT Assay

Rabbit blood was collected from an indwelling catheter in a ear artery into plastic containers. Human blood was collected via venipuncture into vacutainers, some of which contained 0.5 mL of 3.8% citrate. ACT was measured as described in Example 19. Blood samples were mixed with varying concentrations of test compounds dissolved in physiological saline (30 μL for non-citrated blood and 15 μL for citrated blood). Non-citrated blood was used in the assay immediately upon its collection. Citrated blood was kept at ambient temperature for 0.5 to 2 hours and then incubated at 37° C. before used.

Proceeding as described in Example 21, compounds of the present Invention were assayed and found to increased ACT.

Example 22

The following are representative pharmaceutical formulations containing a compound of Formula I.

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of Formula I | 1% |
| Microcrystalline Cellulose | 73% |
| Stearic Acid | 25% |
| Colloidal Silica | 1%. |

What is claimed is:

1. A compound of Formula I:

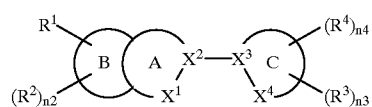

in which:

n2 is 1, 2 or 3;

n3 is 1, 2, 3 or 4;

n4 is 1 or 2;

A together with B form a fused heterobicyclic radical having 8 to 12 annular atoms, wherein each ring has 5 to 7 annular atoms, said annular atoms are selected from C, N, $NR^5$, O and S, wherein $R^5$ is $R^6$ or $X^6R6^a$, wherein $X^6$ is a linking group containing 1 to 12 contiguous linking atoms and $R^6$ and $R^{6a}$ independently represent hydrogen, $(C_{6-14})$aryl, cyclo$(C_{3-14})$alkyl, hetero$(C_{5-14})$aryl, heterocyclo$(C_{3-14})$alkyl, hetero$(C_{8-14})$polycycloaryl or $(C_{9-14})$polycycloaryl, wherein said $R^6$ and $X^6R^{6a}$ groups optionally are substituted with 1 to 5 substituents independently selected from $(C_{1-6})$alkyl, $(C_{1-6})$alkylamino, di$(C_{1-6})$alkylamino, $(C_{1-6})$alkylcarbamoyl, di$(C_{1-6})$alkylcarbamoyl, $(C_{1-6})$alkyloxy, $(C_{1-6})$alkyloxycarbonyl, $(C_{1-6})$alkylsulfinyl, $(C_{1-6})$alkylsulfonyl, $(C_{1-6})$alkylthio, amino, carbamoyl, carboxy, cyano, guanidino, halo, hydroxy, mercapto, perhalo$(C_{1-3})$alkyl, perhalo$(C_{1-3})$alkyloxy, uriedo and $(C_{1-3})$alkylimino;

ring C represents a heteromonocyclic or fused heteropolycyclic ring having 5 to 18 annular atoms, wherein each ring has 5 to 7 annular atoms, said annular atoms are selected from C, N, $NR^5$, O and S, wherein $R^5$ is as defined above;

$X^3$ represents a carbon atom;

$R^1$ is amidino;

each $R^2$ is independently hydrogen, $(C_{1-3})$alkyl, $(C_{1-3})$alkyloxy, $(C_{1-3})$alkylsulfonyl, $(C_{1-3})$alkylthio, carboxy, halo, $(C_{2-12})$heteroalkyl, hydroxy, mercapto or nitro;

each $R^3$ is independently hydrogen, cyano, halo, nitro, perhalo$(C_{1-3})$alkyl or perhalo$(C_{1-3})$alkyloxy; and $R^4$ independently at each occurance represents $C_{4-12}$alkyl substituted with 1 to 5 substituents independently selected from $(C_{1-6})$alkyl, $(C_{1-6})$alkylamino, di$(C_{1-6})$alkylamino, $(C_{1-6})$alkylcarbamoyl, di$(C_{1-6})$alkylcarbamoyl, $(C_{1-6})$alkyloxy, $(C_{1-6})$alkyloxycarbonyl, $(C_{1-6})$alkylsulfinyl, $(C_{1-6})$alkylsulfonyl, $(C_{1-6})$alkylthio, amino, carbamoyl, carboxy, cyano, guanidino, halo, hydroxy, mercapto, perhalo$(C_{1-3})$alkyl, perhalo$(C_{1-3})$alkyloxy, uriedo and $(C_{1-3})$alkylimino, $R^7$ or $X^7R^{7a}$, wherein $X^7$ is a linking group having 1 to 12 contiguous linking atoms and $R^7$ and $R^{7a}$ independently at each occurance represent ($C_{6-14}$)aryl, cyclo($C_{3-14}$)alkyl, hetero($C_{5-14}$)aryl, heterocyclo($C_{3-14}$)alkyl, hetero($C_{8-14}$)polycycloaryl or ($C_{9-14}$)polycycloaryl, and wherein said $R^7$ and $X^7R^{7a}$ groups optionally are substituted with 1 to 5 substituents independently selected from ($C_{1-6}$)alkyl, ($C_{1-6}$) alkylamino, di($C_{1-6}$)alkylamino, ($C_{1-6}$)alkylcarbamoyl, di($C_{1-6}$)alkylcarbamoyl, ($C_{1-6}$)alkyloxy, ($C_{1-6}$) alkyloxycarbonyl, ($C_{1-6}$)alkylsulfinyl, ($C_{1-6}$) alkylsulfonyl, ($C_{1-6}$)alkylthio, amino, carbamoyl, carboxy, cyano, guanidino, halo, hydroxy, mercapto, perhalo($C_{1-3}$)alkyl, perhalo($C_{1-3}$)alkyloxy, uriedo and ($C_{1-3}$)alkylimino; and the individual isomers, mixtures of isomers and pharmaceutically acceptable salts thereof.

2. The compound of claim 1 in which:

n4 is 1;

A together with B form a fused heterobicyclic ring having 8 to 10 annular atoms, wherein each ring has 5 to 6 annular atoms;

ring C is a heteromonocyclic or fused heteropolycyclic ring having from 5 to 18 annular atoms, wherein each ring 5 to 6 annular atoms;

$R^2$ is hydrogen, ($C_{1-3}$)alkyloxy, halo or hydroxy;

each $R^3$ is independently hydrogen, cyano, halo, nitro or perhalo($C_{1-3}$)alkyl;

$X^7$ contains 1 to 10 contiguous linking atoms;

$R^4$ independently at each occurance is selected from a group consisting of ($C_{4-10}$)alkyl, $R^7$ or $X^7R^{7a}$, wherein $X^7$ is a linking group having 1 to 10 contiguous linking atoms $R^7$ and $R^{7a}$ independently represent ($C_{6-10}$)aryl, cyclo($C_{3-6}$)alkyl, hetero($C_{5-10}$)aryl, heterocyclo($C_{5-6}$)alkyl or hetero($C_{8-10}$)polycycloaryl; and $R^5$ is $R^6$ or $X^6R^{6a}$, wherein $X^6$ is a linking group having 1 to 10 contiguous linking atoms and $R^6$ and $R^{6a}$ independently represent hydrogen, ($C_{6-10}$)aryl, cyclo ($C_{3-6}$)alkyl, hetero($C_{5-10}$)aryl, heterocyclo($C_{5-6}$)alkyl or hetero($C_{8-10}$)polycycloaryl; and the individual isomers, mixture of isomers and pharmaceutically acceptable salts thereof.

3. The compound of claim 2 which is a compound of Formula II:

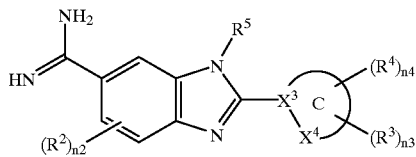

II in which C is a heteromonocyclic or fused heterobicyclic radical containing 5 to 10 annular atoms and $R^5$ is hydrogen or ($C_{1-6}$)alkyl; and the individual isomers, mixture of isomers and pharmaceutically acceptable salts thereof.

4. The compound of claim 3 selected from:

6-(5-amidino-1H-benzimidazol-2-yl)-N-[2-(3-bromo4-methoxyphenyl)ethyl]pyridine-5-carboxamide;

2-(5-amidino-1H-benzimidazol-2-yl)imidazol-1-yl-N-[2-(4-chlorophenyl)ethyl]acetamide;

2-(1-benzyl-1H-imidazol-2-yl)-1H-benzimidazole-5-carboxamidine;

2-(5-butylpyridin-2-yl-1H-benzimidazole-5-carboxamidine;

6-(5-amidino-1H-benzimidazol-2-yl)-N-[2-(4-methoxyphenyl)ethyl]pyridine-5-carboxamide;

2-(1-butyl-1H-imidazol-2-yl)-1H-benzimidazole-5-carboxamidine;

2-{1-[3-(1,3-dioxo-1,3-dihydroisoindol-2-yl)propyl]-5-methyl-1H-imidazol-4-yl}-1H-benzimidazole-5-carboxamidine;

ethyl 2-(5-amidino-1H-benzimidazol-2-yl)imidazol-1-ylacetate;

4-[2-(5-amidino-1H-benzimidazol-2-yl)imidazol-1-yl]-N-[2-(4-chlorophenyl)ethyl]butyramide;

6-(5-amidino-1H-benzimidazol-2-yl)-N-[2-(3,4-dichlorophenyl)ethyl]pyridine-5-carboxamide;

2-[1-(3-morpholin-4-ylcarbonylpropyl)-1H-imidazol-2-yl]-1H-benzimidazole-5-carboxamidine;

2-(5-amidino-1H-benzimidazol-2-yl)imidazol-1-yl-N-[2-(4-hydroxyphenyl)ethyl]acetamide;

2-{1-[4-(1,3-dioxo-1,3-dihydroisoindol-2-yl)butyl]-1H-imidazol-2-yl }-1H-benzimidazole-5-carboxamidine;

2-(5-amidino-1H-benzimidazol-2-yl)imidazol-1-yl-N-(2-naphth-1-ylethyl)acetamide;

2-(5-methyl-1-propyl-1H-imidazol-4-yl)-1H-benzimidazole-5-carboxamidine;

6-(5-amidino-1H-benzimidazol-2-yl)-N-[2-(4-methylphenyl)ethyl]pyridine-5-carboxamide; and 2-(5-methyl-1-benzyl-1H-imidazol-4-yl)-1H-benzimidazole-5-carboxamidine; and the individual isomers, mixture of isomers and pharmaceutically acceptable salts thereof.

5. A pharmaceutical composition comprising a therapeutically effective amount of the compound of claim 1; or an individual isomer, mixture of isomers or pharmaceutically acceptable salt thereof with a pharmaceutically acceptable carrier.

6. A method of treating a disease in an animal in which factor Xa activity contributes to the pathology and/or symptomatology of the disease, which method comprises administering to the animal a therapeutically effective amount a of compound of Formula I:

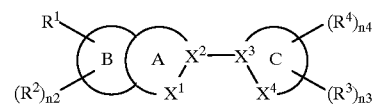

1 in which:

n2 is 1, 2 or 3;

n3 is 1, 2, 3 or 4;

n4 is 1 or 2;

A together with B forms a fused heterobicyclic radical having 8 to 12 annular atoms, wherein each ring has 5 to 7 annular atoms, said annular atoms are selected from C, N, $NR^5$, O and S, wherein $R^5$ is $R^6$ or $X^6R6^a$, wherein $X^6$ is a linking group containing 1 to 12 contiguous linking atoms and $R^6$ and $R^{6a}$ independently represent hydrogen, ($C_{6-14}$)aryl, cyclo($C_{3-14}$) alkyl, hetero($C_{5-14}$)aryl, heterocyclo($C_{3-14}$)alkyl, hetero($C_{8-14}$)polycycloaryl or ($C_{9-14}$)polycycloaryl, wherein said $R^6$ and $X^6R^{6a}$ groups optionally are substituted with 1 to 5 substituents independently selected from ($C_{1-6}$)alkyl, ($C_{1-6}$)alkylamino, di($C_{1-6}$) alkylamino, ($C_{1-6}$)alkylcarbamoyl, di($C_{1-6}$) alkylcarbamoyl, ($C_{1-6}$)alkyloxy, ($C_{1-6}$) alkyloxycarbonyl, ($C_{1-6}$)alkylsulfinyl, ($C_{1-6}$) alkylsulfonyl, ($C_{1-6}$)alkylthio, amino, carbamoyl, carboxy, cyano, guanidino, halo, hydroxy, mercapto, perhalo($C_{1-3}$)alkyl, perhalo($C_{1-3}$)alkyloxy, uriedo and ($C_{1-3}$)alkylimino;

ring C represents a heteromonocyclic or fused heteropolycyclic ring having 5 to 18 annular atoms, wherein each ring has 5 to 7 annular atoms, said annular atoms are selected from C, N, $NR^5$, O and S, wherein $R^5$ is as defined above;

$X^3$ represents a carbon atom;

$R^1$ is amidino;

each $R^2$ is independently hydrogen, ($C_{1-3}$)alkyl, ($C_{1-3}$)alkyloxy, ($C_{1-3}$)alkylsulfonyl, ($C_{1-3}$)alkylthio, carboxy, halo, ($C_{2-12}$)heteroalkyl, hydroxy, mercapto or nitro;

each $R^3$ is independently hydrogen, cyano, halo, nitro, perhalo($C_{1-3}$)alkyl or perhalo($C_{1-3}$)alkyloxy; and $R^4$ independently at each occurance represents $C_{4-12}$ alkyl substituted with 1 to 5 substituents independently selected from ($C_{1-6}$)alkyl, ($C_{1-6}$)alkylamino, di($C_{1-6}$)alkylamino, ($C_{1-6}$)alkylcarbamoyl, di($C_{1-6}$)alkylcarbamoyl, ($C_{1-6}$)alkyloxy, ($C_{1-6}$)alkyloxycarbonyl, ($C_{1-6}$)alkylsulfinyl, ($C_{1-6}$)alkylsulfonyl, ($C_{1-6}$)alkylthio, amino, carbamoyl, carboxy, cyano, guanidino, halo, hydroxy, mercapto, perhalo($C_{1-3}$)alkyl, perhalo($C_{1-3}$)alkyloxy, uriedo and ($C_{1-3}$)alkylimino, $R^7$ or $X^7R^{7a}$, wherein $X^7$ is a linking group having 1 to 12 contiguous linking atoms and $R^7$ and $R^{7a}$ independently at each occurance represent ($C_{6-14}$)aryl, cyclo($C_{3-14}$)alkyl, hetero($C_{5-14}$)aryl, heterocyclo($C_{3-14}$)alkyl, hetero($C_{8-14}$)polycycloaryl or ($C_{9-14}$)polycycloaryl, and wherein said $R^7$ and $X^7R^{7a}$ groups optionally are substituted with 1 to 5 substituents independently selected from ($C_{1-6}$)alkyl, ($C_{1-6}$)alkylamino, di($C_{1-6}$)alkylamino, ($C_{1-6}$)alkylcarbamoyl, di($C_{1-6}$)alkylcarbamoyl, ($C_{1-6}$)alkyloxy, ($C_{1-6}$)alkyloxycarbonyl, ($C_{1-6}$)alkylsulfinyl, ($C_{1-6}$)alkylsulfonyl, ($C_{1-6}$)alkylthio, amino, carbamoyl, carboxy, cyano, guanidino, halo, hydroxy, mercapto, perhalo($C_{1-3}$)alkyl, perhalo($C_{1-3}$)alkyloxy, uriedo and ($C_{1-3}$)alkylimino; and the individual isomers, mixtures of isomers and pharmaceutically acceptable salts thereof.

* * * * *